(12) United States Patent  (10) Patent No.: US 7,632,308 B2
Loulmet (45) Date of Patent: Dec. 15, 2009

(54) METHODS, DEVICES, AND KITS FOR TREATING MITRAL VALVE PROLAPSE

(76) Inventor: Didier Loulmet, 50E 78th St., Apt. 10D, New York, NY (US) 10021

( * ) Notice: Subject to any disclaimer, the term of this patent is extended or adjusted under 35 U.S.C. 154(b) by 695 days.

(21) Appl. No.: 11/286,037

(22) Filed: Nov. 23, 2005

(65) Prior Publication Data

US 2007/0118213 A1 May 24, 2007

(51) Int. Cl.
*A61F 2/24* (2006.01)
*A61F 2/00* (2006.01)
*A61F 13/00* (2006.01)

(52) U.S. Cl. .......................................... 623/2.1; 600/37
(58) Field of Classification Search ................. 623/2.1, 623/2.11, 2.36, 2.37; 600/37
See application file for complete search history.

(56) References Cited

U.S. PATENT DOCUMENTS

| | | | |
|---|---|---|---|
| 3,166,072 A | 1/1965 | Sullivan, Jr. et al. |
| 3,704,711 A | 12/1972 | Park |
| 4,204,283 A | 5/1980 | Bellhouse et al. |
| 4,259,959 A | 4/1981 | Walker |
| 4,492,229 A | 1/1985 | Grunwald |
| 4,524,771 A | 6/1985 | McGregor et al. |
| 4,639,252 A | 1/1987 | Kelly et al. |
| 4,655,773 A | 4/1987 | Grassi |
| 4,731,075 A | 3/1988 | Gallo Mezo et al. |
| 4,816,339 A | 3/1989 | Tu et al. |
| 4,841,888 A | 6/1989 | Mills et al. |
| 4,938,760 A | 7/1990 | Burton et al. |
| 5,013,316 A | 5/1991 | Goble et al. |
| 5,059,201 A | 10/1991 | Asnis |
| 5,101,592 A | 4/1992 | Merritt |
| 5,108,420 A | 4/1992 | Marks |
| 5,125,926 A | 6/1992 | Rudko et al. |

(Continued)

FOREIGN PATENT DOCUMENTS

WO   WO-90/09763 A1   9/1990

(Continued)

OTHER PUBLICATIONS

International Search Report mailed on May 1, 2007 for PCT Application No. PCT/US06/44655 filed on Nov. 15, 2006, three pages.

(Continued)

*Primary Examiner*—Thomas J Sweet
*Assistant Examiner*—Yashita Sharma
(74) *Attorney, Agent, or Firm*—Morrison & Foerster LLP

(57) ABSTRACT

Described here are methods, devices, and kits for treating a prolapsed valve leaflet. The devices generally comprise a flexible cord, a first anchor attached to the cord at its distal end, and a second anchor slidably attached to the cord. The first anchor may be configured to secure the cord to cardiac tissue located below a prolapsed valve leaflet and the second anchor may be configured to secure into the prolapsed valve leaflet. Also described are methods for treating a prolapsed valve including the steps of securing a first anchor to cardiac tissue located below the prolapsed mitral valve leaflet, securing a second anchor to the prolapsed mitral valve leaflet, tensioning a cord connecting the two anchors and securing the cord. Kits including the described devices are also provided.

4 Claims, 17 Drawing Sheets

U.S. PATENT DOCUMENTS

| | | |
|---|---|---|
| 5,171,252 A | 12/1992 | Friedland |
| 5,222,508 A | 6/1993 | Contarini |
| 5,224,946 A | 7/1993 | Hayhurst et al. |
| 5,236,445 A | 8/1993 | Hayhurst et al. |
| 5,258,016 A | 11/1993 | DiPoto et al. |
| 5,275,162 A | 1/1994 | Edwards et al. |
| 5,281,218 A | 1/1994 | Imran |
| 5,284,488 A | 2/1994 | Sideris |
| 5,290,300 A | 3/1994 | Cosgrove et al. |
| 5,304,184 A | 4/1994 | Hathaway et al. |
| 5,334,217 A | 8/1994 | Das |
| 5,336,252 A | 8/1994 | Cohen |
| 5,354,298 A | 10/1994 | Lee et al. |
| 5,374,275 A | 12/1994 | Bradley et al. |
| 5,380,334 A | 1/1995 | Torrie et al. |
| 5,383,897 A | 1/1995 | Wholey |
| 5,403,329 A | 4/1995 | Hinchcliffe |
| 5,417,699 A | 5/1995 | Klein et al. |
| 5,423,856 A | 6/1995 | Green |
| 5,425,744 A | 6/1995 | Fagan et al. |
| 5,431,666 A | 7/1995 | Sauer et al. |
| 5,433,727 A | 7/1995 | Sideris |
| 5,443,446 A | 8/1995 | Shturman |
| 5,450,860 A | 9/1995 | O'Connor |
| 5,454,807 A | 10/1995 | Lennox et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitfield et al. |
| 5,476,470 A | 12/1995 | Fitzgibbons, Jr. |
| 5,480,403 A | 1/1996 | Lee et al. |
| 5,489,298 A | 2/1996 | Love et al. |
| 5,489,498 A | 2/1996 | Ohno et al. |
| 5,492,119 A | 2/1996 | Abrams |
| 5,496,332 A | 3/1996 | Sierra et al. |
| 5,496,336 A | 3/1996 | Cosgrove et al. |
| 5,499,991 A | 3/1996 | Garman et al. |
| 5,501,691 A | 3/1996 | Goldrath |
| 5,507,811 A | 4/1996 | Koike et al. |
| 5,520,700 A | 5/1996 | Beyar et al. |
| 5,527,321 A | 6/1996 | Hinchliffe |
| 5,527,322 A | 6/1996 | Klein et al. |
| 5,527,342 A | 6/1996 | Pietrzak et al. |
| 5,540,704 A | 7/1996 | Gordon et al. |
| 5,542,917 A | 8/1996 | Nita et al. |
| 5,562,686 A | 10/1996 | Sauer et al. |
| 5,562,688 A | 10/1996 | Riza |
| 5,573,540 A | 11/1996 | Yoon |
| 5,578,045 A | 11/1996 | Das |
| 5,582,616 A | 12/1996 | Bolduc et al. |
| 5,584,859 A | 12/1996 | Brotz |
| 5,601,558 A | 2/1997 | Torrie et al. |
| 5,609,598 A | 3/1997 | Laufer et al. |
| 5,613,974 A | 3/1997 | Andreas et al. |
| 5,613,975 A | 3/1997 | Christy |
| 5,632,752 A | 5/1997 | Buelna |
| 5,639,276 A | 6/1997 | Weinstock et al. |
| 5,643,317 A | 7/1997 | Pavcnik et al. |
| 5,643,320 A | 7/1997 | Lower et al. |
| 5,662,654 A | 9/1997 | Thompson |
| 5,662,663 A | 9/1997 | Shallman |
| 5,662,683 A | 9/1997 | Kay |
| 5,667,513 A | 9/1997 | Torrie et al. |
| 5,673,695 A | 10/1997 | McGee et al. |
| 5,679,005 A | 10/1997 | Einstein |
| 5,683,402 A | 11/1997 | Cosgrove et al. |
| 5,700,273 A | 12/1997 | Buelna et al. |
| 5,702,421 A | 12/1997 | Schneidt |
| 5,713,903 A | 2/1998 | Sander et al. |
| 5,720,753 A | 2/1998 | Sander et al. |
| 5,724,978 A | 3/1998 | Tenhoff |
| 5,725,521 A | 3/1998 | Mueller |
| 5,725,552 A | 3/1998 | Kotula et al. |
| 5,732,707 A | 3/1998 | Widder et al. |
| 5,741,297 A | 4/1998 | Simon |
| 5,752,963 A | 5/1998 | Allard et al. |
| 5,766,234 A | 6/1998 | Chen et al. |
| 5,769,846 A | 6/1998 | Edwards et al. |
| 5,776,189 A | 7/1998 | Khalid |
| 5,779,719 A | 7/1998 | Klein et al. |
| 5,792,152 A | 8/1998 | Klein et al. |
| 5,797,960 A | 8/1998 | Stevens et al. |
| 5,810,847 A | 9/1998 | Laufer et al. |
| 5,810,849 A | 9/1998 | Kontos |
| 5,814,070 A | 9/1998 | Borzone et al. |
| 5,817,110 A | 10/1998 | Kronner |
| 5,823,342 A | 10/1998 | Caudillo et al. |
| 5,823,956 A | 10/1998 | Roth et al. |
| 5,824,067 A | 10/1998 | Gross |
| 5,827,203 A | 10/1998 | Nita |
| 5,827,268 A | 10/1998 | Laufer |
| 5,829,447 A | 11/1998 | Stevens et al. |
| 5,830,145 A | 11/1998 | Tenhoff |
| 5,836,955 A | 11/1998 | Buelna et al. |
| 5,846,261 A | 12/1998 | Kotula et al. |
| D404,128 S | 1/1999 | Huebner |
| 5,855,552 A | 1/1999 | Houser et al. |
| 5,855,614 A | 1/1999 | Stevens et al. |
| 5,860,920 A | 1/1999 | McGee et al. |
| 5,860,991 A | 1/1999 | Klein et al. |
| 5,861,003 A | 1/1999 | Latson et al. |
| 5,868,749 A | 2/1999 | Reed |
| 5,868,762 A | 2/1999 | Cragg et al. |
| 5,888,247 A | 3/1999 | Benetti |
| 5,895,404 A | 4/1999 | Ruiz |
| 5,910,155 A | 6/1999 | Ratcliff et al. |
| 5,928,224 A | 7/1999 | Laufer |
| 5,944,738 A | 8/1999 | Amplatz et al. |
| 5,944,739 A | 8/1999 | Zlock et al. |
| 5,947,125 A | 9/1999 | Benetti |
| 5,947,997 A | 9/1999 | Pavcnik et al. |
| 5,948,000 A | 9/1999 | Larsen et al. |
| 5,948,001 A | 9/1999 | Larsen |
| 5,954,732 A | 9/1999 | Hart et al. |
| 5,957,916 A | 9/1999 | Jeevanandam et al. |
| 5,968,047 A | 10/1999 | Reed |
| 5,972,030 A | 10/1999 | Garrison et al. |
| 5,989,284 A | 11/1999 | Laufer |
| 5,993,459 A | 11/1999 | Larsen et al. |
| 5,997,534 A | 12/1999 | Tu et al. |
| 5,997,554 A | 12/1999 | Thompson |
| 6,004,269 A | 12/1999 | Crowley et al. |
| 6,010,531 A | 1/2000 | Donlon et al. |
| 6,012,457 A | 1/2000 | Lesh |
| 6,013,083 A | 1/2000 | Bennett |
| 6,014,589 A | 1/2000 | Farley et al. |
| 6,019,768 A | 2/2000 | Wenstrom, Jr. et al. |
| 6,036,690 A | 3/2000 | De La Plaza Fernandez |
| 6,056,743 A | 5/2000 | Ellis et al. |
| 6,068,648 A | 5/2000 | Cole et al. |
| 6,074,395 A | 6/2000 | Trott et al. |
| 6,077,281 A | 6/2000 | Das |
| 6,077,291 A | 6/2000 | Das |
| 6,079,414 A | 6/2000 | Roth |
| 6,086,591 A | 7/2000 | Bojarski |
| 6,086,612 A | 7/2000 | Jansen |
| 6,096,060 A | 8/2000 | Fitts et al. |
| 6,113,631 A | 9/2000 | Jansen |
| 6,120,453 A | 9/2000 | Sharp |
| 6,126,682 A | 10/2000 | Sharkey et al. |
| 6,146,387 A | 11/2000 | Trott et al. |
| 6,149,660 A | 11/2000 | Laufer et al. |
| 6,152,144 A | 11/2000 | Lesh |
| 6,152,935 A | 11/2000 | Kammerer et al. |

| | | |
|---|---|---|
| 6,159,235 A | 12/2000 | Kim |
| 6,161,543 A | 12/2000 | Cox et al. |
| 6,165,183 A | 12/2000 | Kuehn et al. |
| 6,167,889 B1 | 1/2001 | Benetti |
| 6,174,287 B1 | 1/2001 | Resnick et al. |
| 6,187,040 B1 | 2/2001 | Wright |
| 6,206,886 B1 | 3/2001 | Bennett |
| 6,231,561 B1 | 5/2001 | Frazier et al. |
| 6,245,079 B1 | 6/2001 | Nobles et al. |
| 6,269,819 B1 | 8/2001 | Oz et al. |
| 6,270,515 B1 | 8/2001 | Linden et al. |
| 6,280,448 B1 | 8/2001 | Trott et al. |
| 6,283,962 B1 | 9/2001 | Tu et al. |
| 6,283,993 B1 | 9/2001 | Cosgrove et al. |
| 6,290,674 B1 | 9/2001 | Roue et al. |
| 6,290,702 B1 | 9/2001 | Fucci et al. |
| 6,306,133 B1 | 10/2001 | Tu et al. |
| 6,311,623 B1 | 11/2001 | Zaruba |
| 6,319,270 B1 | 11/2001 | Grafton et al. |
| 6,332,468 B1 | 12/2001 | Benetti |
| 6,332,893 B1 | 12/2001 | Mortier et al. |
| 6,334,873 B1 | 1/2002 | Lane et al. |
| 6,344,053 B1 | 2/2002 | Boneau |
| 6,346,074 B1 | 2/2002 | Roth |
| 6,346,109 B1 | 2/2002 | Fucci et al. |
| 6,355,030 B1 | 3/2002 | Aldrich et al. |
| 6,355,052 B1 | 3/2002 | Neuss et al. |
| 6,363,940 B1 | 4/2002 | Krag |
| 6,368,339 B1 | 4/2002 | Amplatz |
| 6,409,759 B1 | 6/2002 | Peredo |
| 6,440,154 B2 | 8/2002 | Gellman et al. |
| 6,451,024 B1 | 9/2002 | Thompson et al. |
| 6,472,983 B1 | 10/2002 | Grunder |
| 6,547,787 B1 | 4/2003 | Altman et al. |
| 6,592,610 B2 | 7/2003 | Beyar |
| 6,599,310 B2 | 7/2003 | Leung et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,702,826 B2 | 3/2004 | Liddicoat et al. |
| 6,718,985 B2 | 4/2004 | Hlavka et al. |
| 6,719,785 B2 | 4/2004 | Schoon et al. |
| 6,740,107 B2 | 5/2004 | Loeb et al. |
| 6,743,239 B1 | 6/2004 | Kuehn et al. |
| 6,746,472 B2 | 6/2004 | Frazier et al. |
| 7,087,064 B1 | 8/2006 | Hyde |
| 7,101,395 B2 | 9/2006 | Tremulis et al. |
| 7,186,262 B2 | 3/2007 | Saadat |
| 7,189,199 B2 | 3/2007 | McCarthy et al. |
| 7,217,284 B2 | 5/2007 | Houser et al. |
| 7,562,660 B2 | 7/2009 | Saadat |
| 2002/0035361 A1 | 3/2002 | Houser et al. |
| 2002/0087048 A1 | 7/2002 | Brock et al. |
| 2002/0087049 A1 | 7/2002 | Brock et al. |
| 2002/0087166 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0161378 A1 | 10/2002 | Downing |
| 2003/0018358 A1 | 1/2003 | Saadat |
| 2003/0078465 A1 | 4/2003 | Pai et al. |
| 2003/0105519 A1 | 6/2003 | Fasol et al. |
| 2003/0105520 A1 * | 6/2003 | Alferness et al. ........... 623/2.36 |
| 2003/0233142 A1 | 12/2003 | Morales et al. |
| 2004/0019378 A1 | 1/2004 | Hlavka et al. |
| 2004/0024414 A1 | 2/2004 | Downing |
| 2004/0133192 A1 | 7/2004 | Houser et al. |
| 2004/0152947 A1 | 8/2004 | Schroeder et al. |
| 2005/0075723 A1 * | 4/2005 | Schroeder et al. ............ 623/2.1 |
| 2005/0197692 A1 | 9/2005 | Pai et al. |
| 2005/0197693 A1 | 9/2005 | Pai et al. |
| 2005/0197694 A1 | 9/2005 | Pai et al. |
| 2006/0287661 A1 | 12/2006 | Bolduc et al. |
| 2006/0287716 A1 | 12/2006 | Banbury et al. |
| 2007/0118154 A1 | 5/2007 | Crabtree |

FOREIGN PATENT DOCUMENTS

| | | |
|---|---|---|
| WO | WO-98/32401 A1 | 7/1998 |
| WO | WO-98/35638 A1 | 8/1998 |
| WO | WO-98/38936 A1 | 9/1998 |
| WO | WO-99/02096 A1 | 1/1999 |
| WO | WO-99/05983 A1 | 2/1999 |
| WO | WO-00/27292 A1 | 5/2000 |
| WO | WO-00/27292 C2 | 5/2000 |
| WO | WO-01/00114 A1 | 1/2001 |
| WO | WO-01/26557 A1 | 4/2001 |
| WO | WO-03/003930 A1 | 1/2003 |
| WO | WO-03/105670 A2 | 12/2003 |
| WO | WO-03/105670 A3 | 12/2003 |
| WO | WO-2005/102181 A1 | 11/2005 |
| WO | WO-2007/061834 A2 | 5/2007 |

OTHER PUBLICATIONS

Hayashi, K. et al. (1997). "The Effect of Thermal Heating on the Length and Histologic Properties of the Glenohumeral Joint Capsule", *The American Journal of Sports Medicine* 25(1):107-112.

Naseef III, G.S. et al. (1997). "The Thermal Properties of Bovine Joint Capsule: The Basic Science of Laser- and Radiofrequency-Induced Capsular Shrinkage", *The American Journal of Sports Medicine* 25(5):670-674.

Selecky, M.T. et al. (1999). "The Effects of Laser-Induced Collagen Shortening on the Biomechanical Properties of the Inferior Glenohumeral Ligament Complex", *The American Journal of Sports Medicine* 27(2):168-172.

* cited by examiner

METHODS, DEVICES, AND KITS FOR TREATING MITRAL VALVE PROLAPSE

FIELD

The methods, devices, and kits described here are in the field of cardiac valve repair, and more specifically, in the field of treating mitral valve prolapse.

BACKGROUND

The mitral valve comprises two leaflets attached to the mitral valve annulus, which are supported towards their free edge by cords (chordae tendinae) fastened to the internal wall of the ventricle and to the papillary muscles. However, sometimes one or both of the valve leaflets become loose, due to failure or loosening of one or several of these cords. The valve then prolapses and its bloodtight seal becomes compromised, causing the blood to flow back into the left atrium during systole.

Some solutions to this prolapse problem have focused on either replacing the whole valve with an artificial one, or repairing the part of the valve that is diseased in order to restore normal function. Other solutions focus on clipping the valve leaflets together in order to obtain better leaflet coaption. Most of these solutions are surgical, as opposed to percutaneous, in nature, requiring an incision into the thoracic cavity (e.g., a median sternotomy) and into the heart. This type of surgery also necessitates arresting the heart, and thus the use of a extracorporeal circulation system such as a heart-lung-bypass machine to take over the heart function while the patient's heart is arrested. This surgery is incredibly invasive, causing high risks and morbidity to those eligible. In addition, the use of a heart-lung-bypass machine poses an inflammatory reaction risk as components of the blood can get activated while circulating in the machines tubes, reservoirs, pumps, and oxygenators, which are made of foreign materials. Because of the risks and invasiveness of the surgery, the recovery time is typically quite lengthy.

Accordingly, it would be advantageous to have methods, devices, and kits for treating mitral valve prolapse, which are less invasive and pose less risks to the patient than typical open heart surgery. It would also be advantageous to have alternative methods and devices for treating mitral valve prolapse.

SUMMARY

Described here are methods, devices, and kits for treating a prolapsed valve leaflet, such as a mitral valve leaflet or a tricuspid valve leaflet. In general, the devices include a flexible cord having a proximal and a distal end, a first anchor, and a second anchor. The first and second anchors may be attached to the cord. Either or both of the first and second anchors may be slideably attached to the flexible cord. Either the first or second anchors may be attached to the distal end of the flexible cord.

In some variations, the devices comprise a flexible cord, having a proximal end and a distal end, a first anchor attached to the cord at its distal end and configured to secure the cord to cardiac tissue located below a prolapsed valve leaflet, and a second anchor slidably attached to the cord and configured to secure into the prolapsed valve leaflet. The cardiac tissue may be selected from the group consisting of a papillary muscle and a ventricular wall according to some variations. As described above, the valve leaflet may be a mitral valve leaflet or a tricuspid valve leaflet.

The second anchor may include two legs that are configured to pierce tissue, and in some variations the second anchor further comprises an eyelet. The first anchor may have a tissue piercing tip, and in some variations, the tip comprises two legs, which may or may not be configured to expand after they are secured into tissue.

At least one of the first or second anchors may be made from a shape memory material, and in some variations, the shape memory material is a nickel titanium alloy. Similarly, the cord may be made from a material selected from the group consisting of non-polymeric fabrics, polymers, and mixtures thereof. In some variations, the cord is made from a non-polymeric fabric and polymer mixture. The devices may further comprise a fastener for securing the second anchor into the prolapsed valve leaflet.

The described methods for treating a prolapsed valve leaflet typically include securing a first anchor to a cardiac tissue located below the prolapsed valve leaflet (wherein the first anchor is attached to a flexible cord), securing a second anchor into the prolapsed valve leaflet (wherein the second anchor is attached to the flexible cord), and tensioning the cord after the first and second anchors have been secured. The position of the prolapsed valve leaflet may be adjusted by coordinating the tension of the cord and the location of the leaflet. For example, a practitioner (e.g., a doctor, surgeon, technician, etc.) may move the prolapsed valve into a correct (e.g., non-prolapsed) position by adjusting the position of the valve leaflet directly by pushing against the anchor attached to the valve leaflet (e.g., using the fastener to push against the anchor and applying tension to the cord). Once the valve leaflet is positioned correctly, the practitioner can secure cord to maintain the correct position of the valve leaflet. The valve leaflet position may be adjusted in real-time in a beating heart (e.g., using echocardiography). For example, the valve leaflet may be repositioned while monitoring mitral regurgitation (MR). Once any MR is reduced or eliminated, the cord can be secured.

Any appropriate prolapsed valve leaflet may be treated as described herein, including mitral valve leaflets and tricuspid valve leaflets. Further, these methods may be performed using one or more catheters or using non-catheter surgical methods, or using a combination of catheter-type surgical methods and non-catheter type surgical methods.

In some variations, the flexible cord may be advanced via one or more catheters to the proximity of the prolapsed valve leaflet in an anterograde approach (e.g., from above the mitral valve). For example, the first anchor can be attached to the distal end of the flexible cord so that it can be secured to the cardiac tissue located below the prolapsed valve leaflet. In this example, the second anchor is slideably attached to the flexible cord, so that it can be secured to the prolapsed valve leaflet. Alternatively, the flexible cord may be advanced via a retrograde approach (e.g., from below the mitral valve). In this variation the first anchor can be attached to the distal end of the flexible cord so that it can be secured to the prolapsed valve leaflet, while the second anchor is slideably attached to the flexible cord, so that it can be secured to the cardiac tissue located below the prolapsed valve leaflet.

In one variation the method provides for treating a prolapsed mitral valve including the steps of advancing a flexible cord (having a first anchor attached at its distal end) to the proximity of a prolapsed mitral valve leaflet, securing the first anchor to cardiac tissue located below the prolapsed mitral valve leaflet, securing a second anchor slidably attached to the cord into the prolapsed mitral valve leaflet, and tensioning the cord and securing the second anchor. In all of the methods described herein, the cardiac tissue located below the prolapsed valve (to which one of the anchors is secured) may be selected from the group consisting of a papillary muscle and a ventricular wall.

These methods may further comprise fixing the cord in its tensioned position, for example, by applying a fastener to the cord. The methods may also comprise cutting the cord, for example, by advancing a looped cutting wire over the cord, positioning the looped cutting wire proximal of the second anchor, and pulling on the cutting wire to cut the cord.

Kits for treating a prolapsed valve leaflet (e.g., a mitral valve leaflet) are also described. In general the kits comprise a flexible cord having a proximal end and a distal end, a first anchor attached to the cord at its distal end, a second anchor for slidable attachment to the cord, and at least one catheter for delivery of the flexible cord to the proximity of the prolapsed valve leaflet. In some variations, the first anchor is configured to secure the cord to cardiac tissue located below a valve leaflet, and the second anchor is configured to secure into a prolapsed valve leaflet.

The kit may further comprise at least one additional catheter, a cutting wire for cutting the cord, a fastener, and/or instructions on how to use the contents of the kit. At least one of the first or second anchors may be made from a shape memory material, for example, a nickel titanium alloy. Similarly, the cord may be made from a material selected from the group consisting of non-polymeric fabrics, polymers, and mixtures thereof. In some variations, the cord is made from a non-polymeric fabric and polymer mixture.

The first anchor may have a tissue piercing tip, and in some variations the tip comprises two legs. In these variations, the legs may be configured to expand after they are secured into tissue.

DETAILED DESCRIPTION

Figure 1:
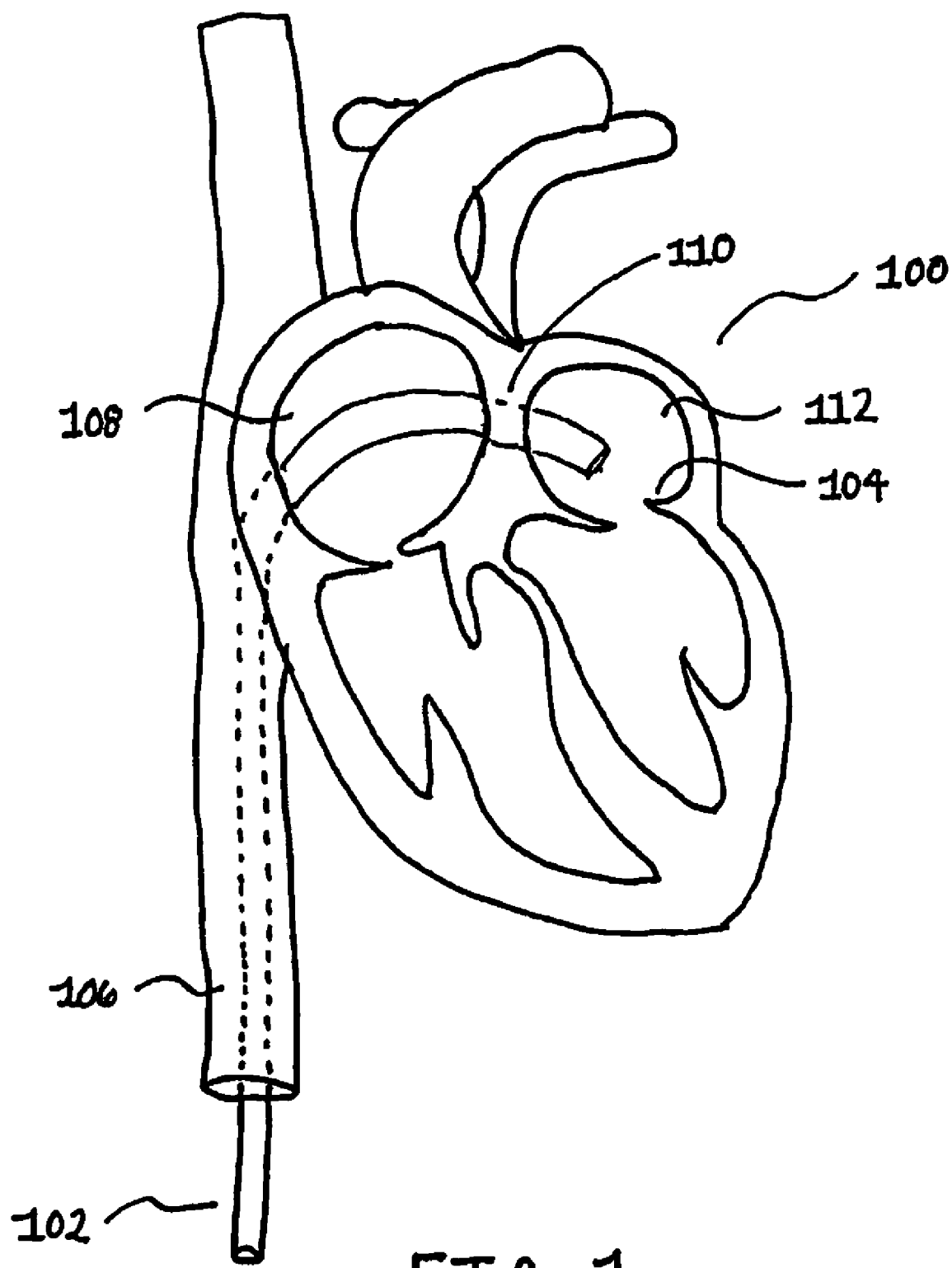
FIG. 1 depicts one method of accessing a prolapsed leaflet of a mitral valve using a trans-septal catheter, in accordance with the methods and devices herein described.

Described here are methods, devices, and kits for treating valve prolapse (such as mitral valve prolapse). In general, the methods, devices, and kits relate to the use of a cord that can be secured into cardiac tissue located below the valve leaflets (e.g., the papillary muscles or the ventricular wall), coupled to a prolapsed valve leaflet, and then tensioned to correct the prolapse. While the majority of the description herein relates to the use of these devices and kits during a percutaneous or intravascular procedure, the devices and kits may also be used during open surgical procedures as well.

Devices

In general, the devices for treating a prolapsed mitral valve leaflet comprise a flexible cord, having a proximal end and a distal end, a first anchor attached to the cord at its distal end, and a second anchor slidably attached to the cord. In some variations, the first anchor is configured to secure the cord to cardiac tissue located below the prolapsed mitral valve leaflet, and the second anchor is configured to secure into the prolapsed mitral valve leaflet. In some variations, the first anchor is configured to secure into the prolapsed mitral valve leaflet, and the second anchor is configured to secure the cord to cardiac tissue located below the prolapsed mitral valve leaflet.

As will be described in more detail below, the first anchor may have a tissue piercing tip, which in some variations comprises two legs that may be configured to expand after securing into cardiac tissue (e.g., a papillary muscle and a ventricular wall). Similarly, the second anchor may comprise two legs that are configured to pierce mitral valve leaflet tissue, and may further comprise an eyelet. Either of the anchors may be made from a shape memory material such as a nickel titanium alloy.

The cord is typically flexible so that it can be maneuvered through a catheter, and may, for example, be made from a material selected from the group consisting of non-polymeric fabrics, polymers, or mixtures thereof. In some variations, the cord is made from a polymeric and non-polymeric fabric mixture, such as a PTFE (polytetrafluoroethylene, including expanded polytetrafluoroethylene) fabric, although any suitable artificial or biological material may be used. It should be noted that the cord is of such a length as to enable it to be manipulated outside of the patient's body. Thus, the suitable length of the cord is determined in large part by the method of access (e.g., less cord will be necessary if the prolapsed mitral valve leaflet is accessed via the jugular rather than the femoral).

The device may further comprise a fastener. In this way, after the cord has been secured into cardiac tissue by the first anchor, and coupled to a prolapsed mitral valve leaflet by a second anchor, it may be pulled tight or tensioned, and fastened in place. For example, the cord may be fastened at a tension that helps correct the valve leaflet prolapse after the valve has been repositioned, as described herein. A more detailed description of the device and all of its optional components will be provided in the discussion of the methods below.

Methods

In general, the methods for treating a prolapsed valve leaflet comprise securing a first anchor to cardiac tissue located below the prolapsed valve leaflet (wherein the first anchor is attached to a flexible cord), securing a second anchor into the prolapsed valve leaflet (wherein the second anchor is attached to the flexible cord), and securing the cord.

When a catheter is used to apply the device to treat a prolapsed valve, the application may be performed either anterograde (e.g., in the usual direction of flow of blood, typically above the valve) or retrograde (e.g., in the direction against the normal flow of blood, typically from blow the valve). Although most of the examples of devices and methods described herein illustrate the anterograde approach, it should be understood that the retrograde approach may also be used.

One variation of the method for treating a prolapsed valve leaflet (e.g., a mitral valve leaflet) comprises advancing a flexible cord having a first anchor attached at its distal end to the proximity of the prolapsed valve leaflet, securing the first anchor to cardiac tissue located below the prolapsed valve leaflet (e.g., papillary muscle or the ventricular wall), securing a second anchor slidably attached to the cord into the prolapsed mitral valve leaflet, and tensioning the cord after the second anchor has been secured into the prolapsed mitral valve leaflet. The prolapse of the valve leaflet may be corrected so that it does not prolapse by moving the valve into the correct non-prolapsed position (e.g., by pushing against the anchor with a fastener, and by tensioning the cord between the anchors so that the valve leaflet does not prolapse). The cord may be secured in using a fastener. The valve leaflet may be moved by manipulating the cord, by using a catheter, a probe, or by any other appropriate positioning step. For example, the distal end of a catheter may be used to position the valve leaflet, or the fastener may be used to position the valve leaflet. In some variations the valve leaflet is manipulated after an anchor has been inserted into (or through) the valve leaflet, but before the tension on the cord is secured by the fastener. Once the leaflet is positioned, the cord may be optimally tensioned to maintain the corrected position, and the cord may be secured into place and cut.

For example, FIG. 1. shows a cross-section of heart (100), having a prolapsed mitral valve leaflet (104). To access the prolapsed mitral valve leaflet (104), a trans-septal catheter (102) is introduced into the inferior vena cava (106), which is in turn accessed through one of the femoral veins. The trans-septal catheter (102) is then advanced up through the right atrium (108) and through the interatrial septum (110). Examples of the trans-septal approach are described in U.S. Pat. Nos. 6,743,239, 6,695,866 (herein incorporated by reference in their entirety). The catheter should be flexible and steerable, so that it can be maneuvered through the tortuous anatomy of the vasculature. For example, the catheter may include a steerable sheath, wherein at least part of the sheath (e.g., the distal end) is steerable in one or more directions. Thus, the sheath may be inserted trans-septally and oriented (e.g., towards the anterior commissure) so that another catheter may pass through the sheath and be further steered towards the valve leaflet and/or the cardiac tissue located beneath prolapsed valve leaflet.

As described above, FIGS. 1-15 depict one method of accessing the prolapsed mitral valve leaflet (104) (e.g., the anterograde approach), however different methods of access are also suitable. For example, a catheter may also be introduced via the jugular vein, may be introduced through the right femoral artery, and advanced up to the left atrium (112) by crossing the aortic valve, or may be introduced via the carotid or subclavian arteries. Thus, the order of the steps described in the method may be adapted to suit these variations. For example, in a retrograde approach the valve is accessed from below, and the distal end of the cord is attached to a first anchor adapted to secure to the valve leaflet, and the second anchor is adapted to secure to the cardiac tissue located beneath prolapsed valve leaflet and be slideably connected to the cord.

Any appropriate visualization technique may be used to help the practitioner visualize the valve anatomy, and to manipulate or steer the catheters. For example, intracardiac echo, or transesophageal echo may be used. Thus, the devices described herein may be adapted to enhance visualization of the devices when used with any of the techniques. For example, the devices may include contrasting agents, and they may include electron dense or radioopaque regions, etc. In addition, rapid ventricular pacing, or adenosine IV administration may allow for transient and reversible cardiac arrest in order to stabilize the leaflets and papillary muscles and facilitate targeting.

Figure 2:
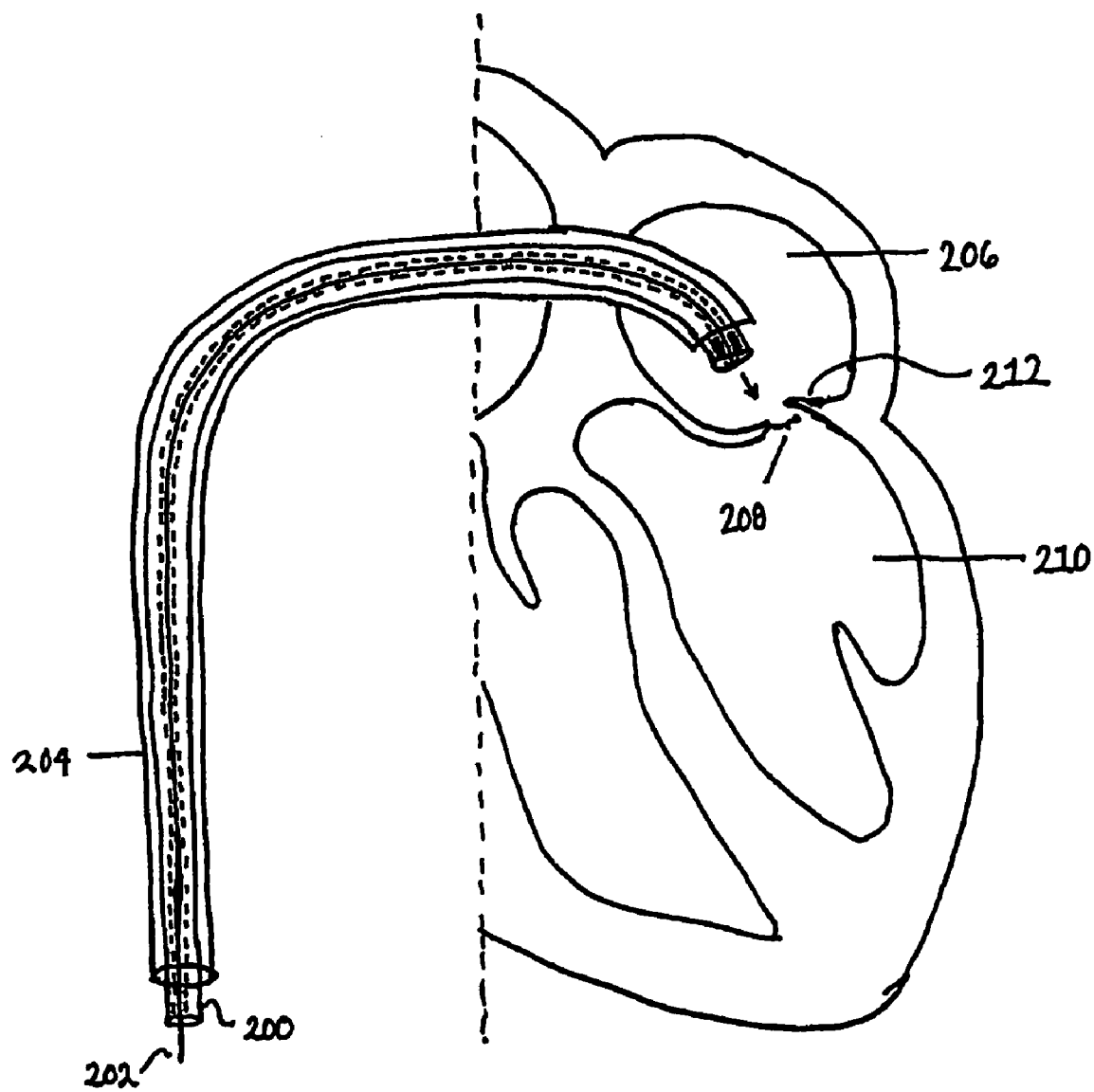
FIG. 2 provides a magnified view of FIG. 1, where a first catheter has been introduced through the trans-septal catheter and into the left atrium.

FIG. 2 provides a magnified view of the heart cross-section of FIG. 1. Shown in FIG. 2 is a catheter (200) introduced into trans-septal catheter (204) (e.g., a trans-septal sheath). Catheter (200) is carrying a flexible cord (202). Catheter (202) is advanced through the trans-septal catheter (204) to the left atrium (206), and down through the mitral valve opening (208), and into the left ventricle (210). In some variations, the trans-septal sheath 204 has a steerable (or directional) tip to help guide the catheter(s) towards the leaflet and cardiac tissue beneath the leaflet. As can be seen in FIG. 2, mitral valve leaflet (212) is prolapsed so that it can no longer prevent the back flow of blood into the left atrium when the ventricle contracts.

Figure 3:
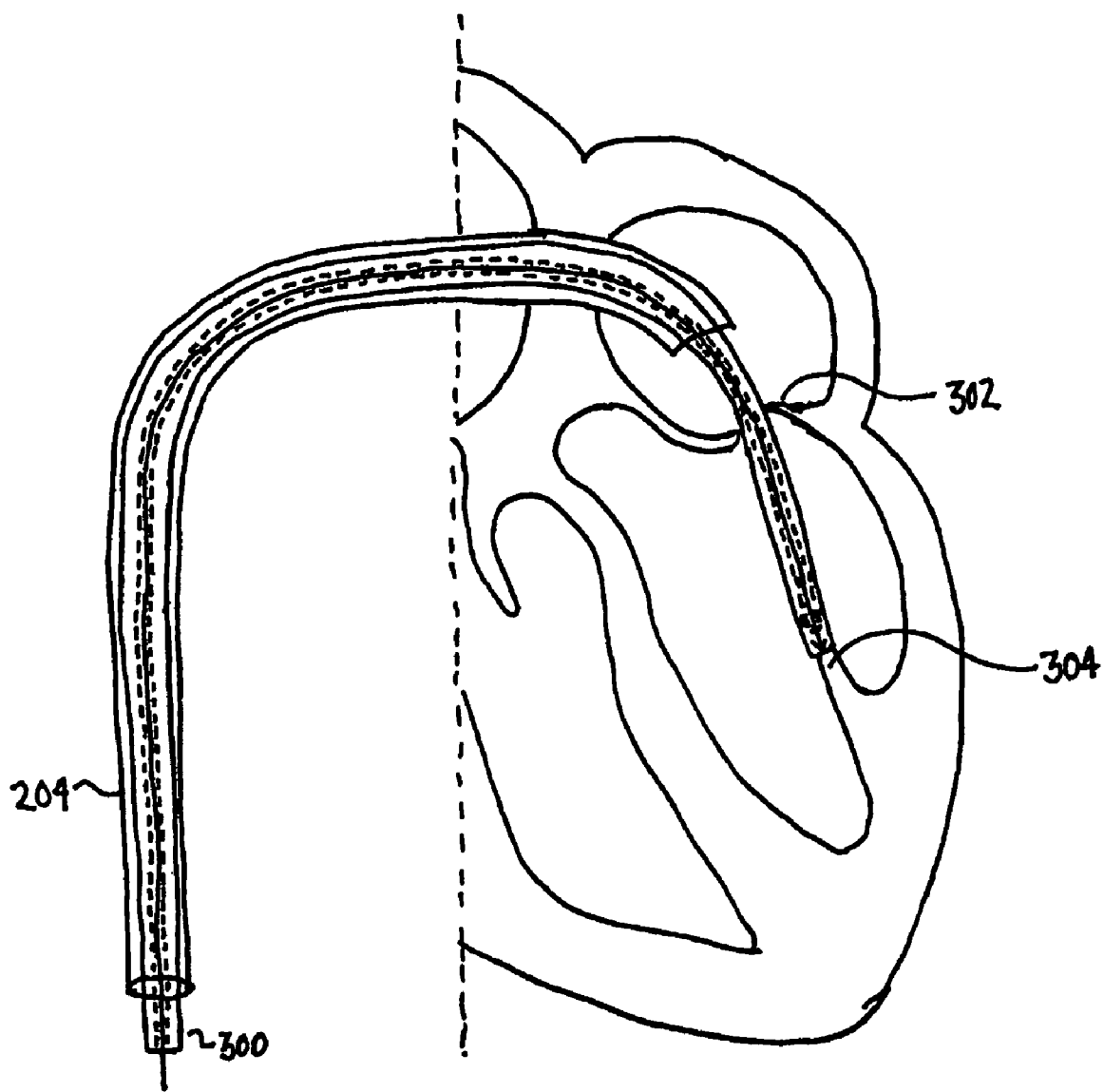
FIG. 3 depicts the application of suction from the first catheter to the papillary muscle.

FIG. 3 shows catheter (300) being advanced to cardiac tissue located beneath prolapsed mitral valve leaflet (302), and specifically to the head of papillary muscle (304). In some variations, the catheter may be steerable (e.g., the tip may be at steerable in at least one direction). Thus, the trans-septal sheath (204) and the catheter together may be used to guide the catheter (300). The catheter (300) is connected to a vacuum source (not shown) located outside of the patient's body. In some variations, the edges of the distal end of catheter (300) are designed so as to maximize contact with the papillary muscle and to minimize aspiration of blood into the catheter during the time suction is applied. For example, the distal end of the catheter may be adapted to conform to the cardiac tissue that it contacts (e.g., the head of the papillary muscle). It should be noted, however, that while FIG. 3 depicts catheter (300) being advanced to the head of papillary muscle 304), that the catheter may be advanced to any suitable cardiac tissue located below the prolapsed mitral valve (302). For example, catheter (300) may be advanced to a location along the side or base of the ventricular wall. That is, the catheter need not be advanced to a location directly vertical of the prolapsed mitral valve leaflet.

Figure 4A:
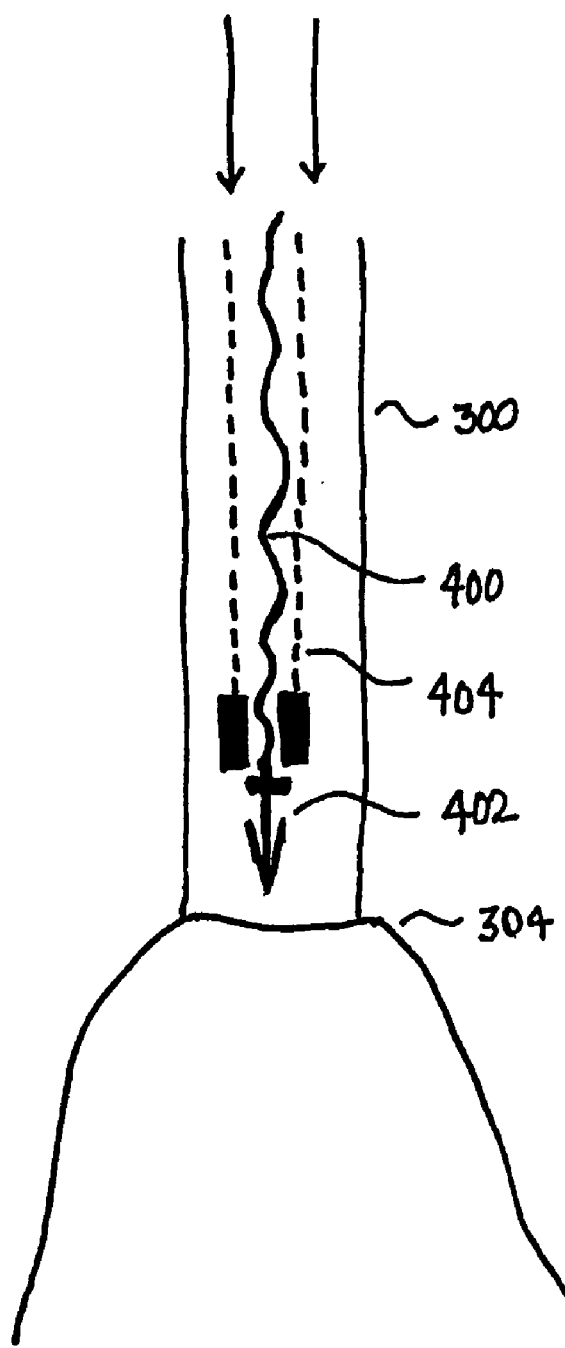
FIG. 4A provides a magnified view of the distal end of the first catheter, which is temporarily adhered to the papillary muscle via suction.

FIG. 4A provides a magnified view of the distal end of the catheter (300) from FIG. 3. As shown there, catheter (300) has been advanced to the head of papillary muscle (304), and is held in place by light suction. In general, adequate suction will be applied to form a seal between the catheter and the head of the papillary muscle. The suction is sufficient to stabilize the catheter to the head of the papillary muscle, but does not damage or otherwise harm the papillary muscle, as would be observed by an ordinary artisan. Catheter (300) is carrying cord (400), which has a first anchor (402) at its distal end. The first anchor (402) may be secured to the cord (400) in any suitable manner. For example, the cord (400) may be tied to first anchor (402), or first anchor (402) may be welded, bonded, or otherwise adhered to cord (400). Also shown is a plunger or piston-like mechanism (404), which when advanced distally (shown by arrows), deploys first anchor (402) out from the distal end of catheter (300) and into the head of papillary muscle (304). The plunger or piston-like mechanism is typically maneuvered by the practitioner, outside of the patient's body. While a plunger, or piston-like mechanism is shown in FIG. 4A, any suitable deployment mechanism may be used to deploy first anchor (402). For example, a hydraulic mechanism may be used, or the anchor may be deployed with the use of an expandable balloon.

Figure 4B:
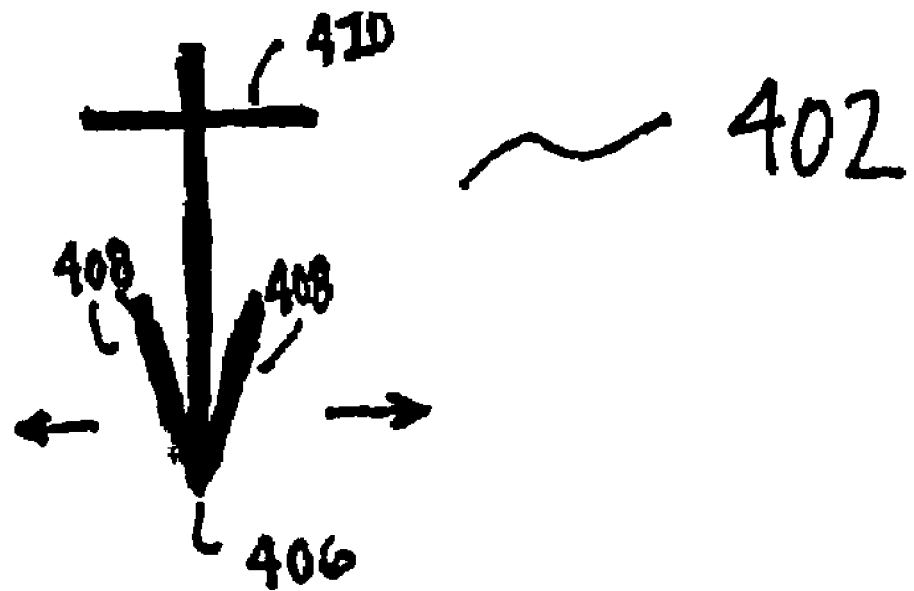
FIG. 4B provides an illustrative example of a suitable first anchor, in accordance with the methods, devices, and kits described herein.
Figure 4B:
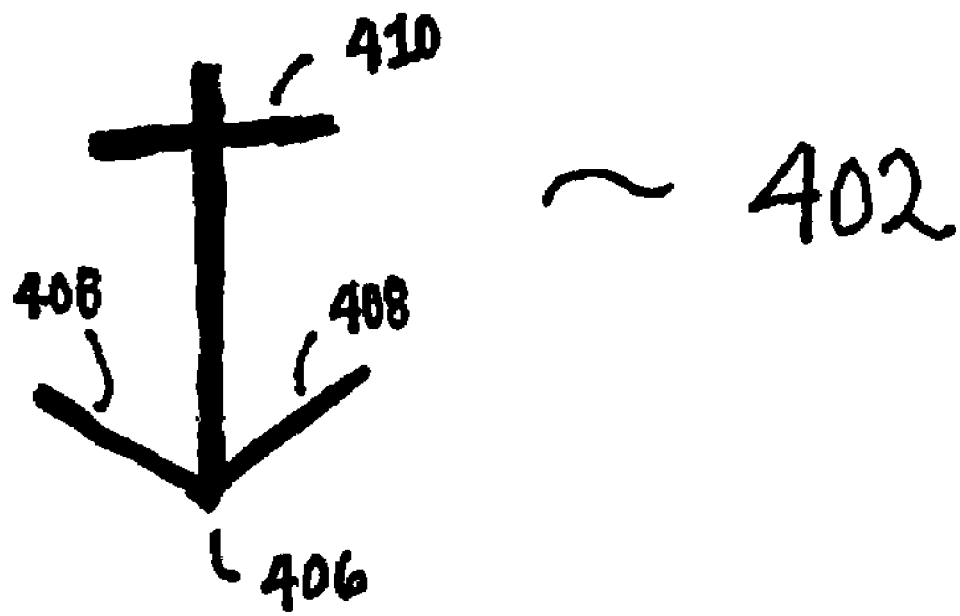

FIG. 4B provides a magnified view of the first anchor (402) shown in an unexpanded (top view) and expanded (bottom view) configuration. As shown by FIG. 4B, first anchor (402) has a tissue piercing tip (406). While the tissue piercing tip (406) of first anchor (402) is shown as being sharp or pointed, it need not be. Indeed, any tip configured to pierce tissue (whether blunt or sharp) is suitable. The tip of first anchor (402) in the variations shown in FIGS. 4A and 4B comprise two legs (408), which are configured to expand after they are secured into cardiac tissue (as shown by the arrows in the top picture in FIG. 4B, and as shown expanded in the bottom picture in FIG. 4B). The legs of the anchors described herein may be extended passively, actively or both to help secure the anchor in the tissue. For example, the legs may be extended actively by releasing them from tension (e.g., compression) or by using a shape-memory alloy, as described above. The legs may be passively extended after insertion into the tissue by pulling "backwards" on the anchor after it has been inserted into the tissue; the legs of the anchor may act as barbs, and expand into the tissue.

First anchor (402) may comprise any suitable number of legs. Indeed, in some variations, it might be preferable for first anchor (402) to have one, two, three or more legs. First anchor (402) is also shown as having a t-bar (410) near its proximal end, although it need not have one. Having a t-bar (410) at its proximal end may help further secure the anchor into cardiac tissue. In some variations the t-bar may provide a surface against which force can be applied to drive the anchor into a tissue. It may also be beneficial to have at least a portion of the first anchor (402) made from a shape memory material such as a nickel titanium alloy. However, any other flexible, yet sturdy, biocompatible material may be used. While first anchor (402) is shown in FIGS. 4A and 4B as having a modified shipping anchor configuration (i.e., having a v-shaped distal end with a t-bar), any suitable configuration may be used. Typically, first anchor (402) is of a size suitable to secure into cardiac tissue. For example, the anchor may be between about 3 and about 12 mm long, or between about 5 and about 10 mm long. In some variations, the anchor may be about 8 mm long. In some variations, the first anchor is longer than it is wide.

Figure 5:
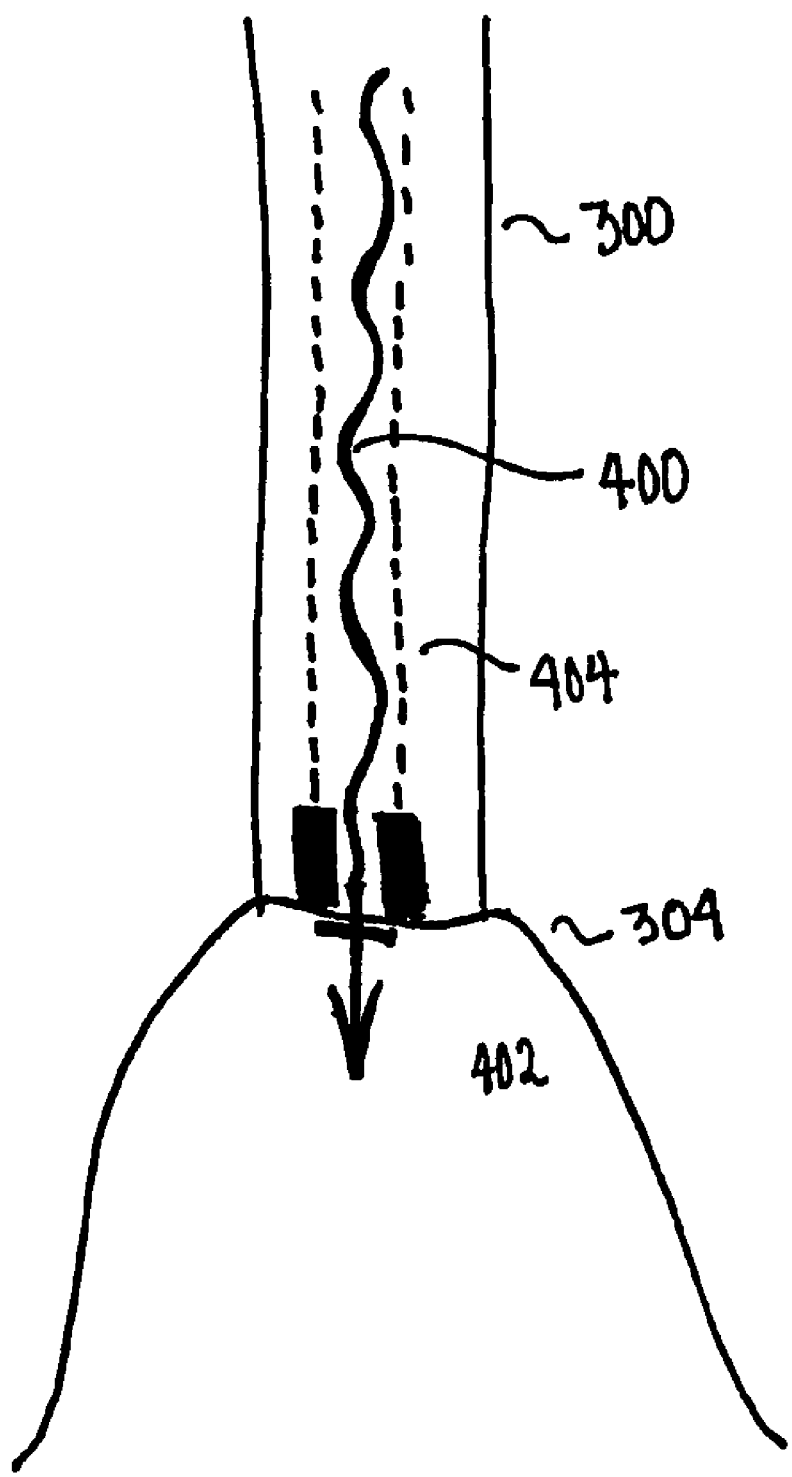
FIG. 5 provides a magnified view of the deployment of the first anchor into the papillary muscle tissue.

FIG. 5 simply demonstrates the first anchor (402) being deployed into the head of papillary muscle (304) by distal advancement of the plunger or piston-like mechanism (404). After the first anchor (402) is fully deployed into the head of papillary muscle (304), its legs may expand to further secure the anchor into the cardiac tissue, as shown in the variation of FIG. 4B. Cord (400) may be pulled proximally to ensure first anchor (402) is firmly and adequately secured to the head of papillary muscle (304) or other cardiac tissue as the case may be. If the anchor is not firmly secured, the deployment mechanism (e.g., hydraulic, plunger, or piston (404)) may be retracted proximally, the anchor withdrawn, and then re-deployed by the deployment mechanism (e.g., by distal advancement of a plunger or piston (404)).

Figure 6:
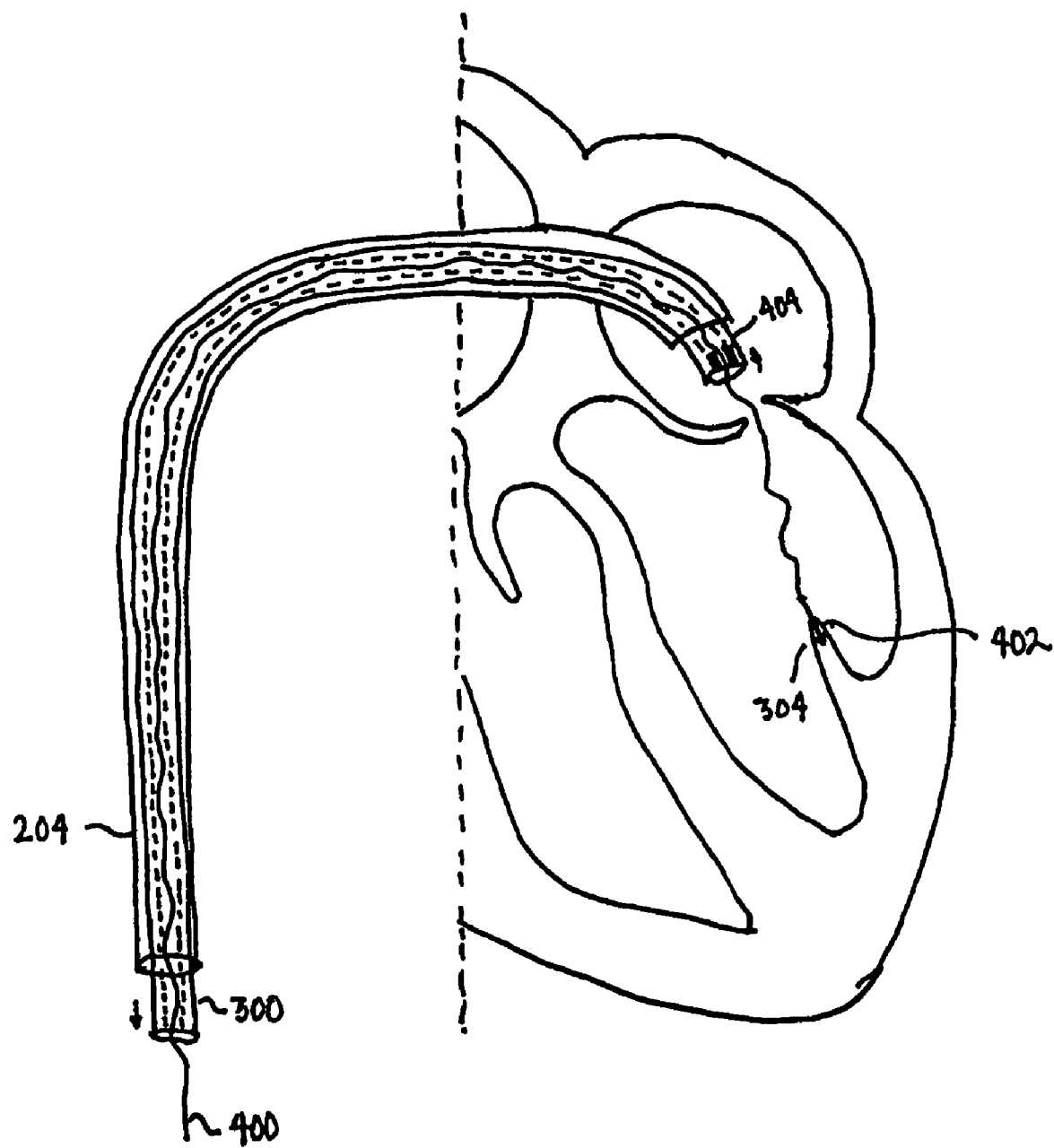
FIG. 6 depicts the cord secured to the papillary muscle via the first anchor, as the first catheter is being removed.
Figure 7:
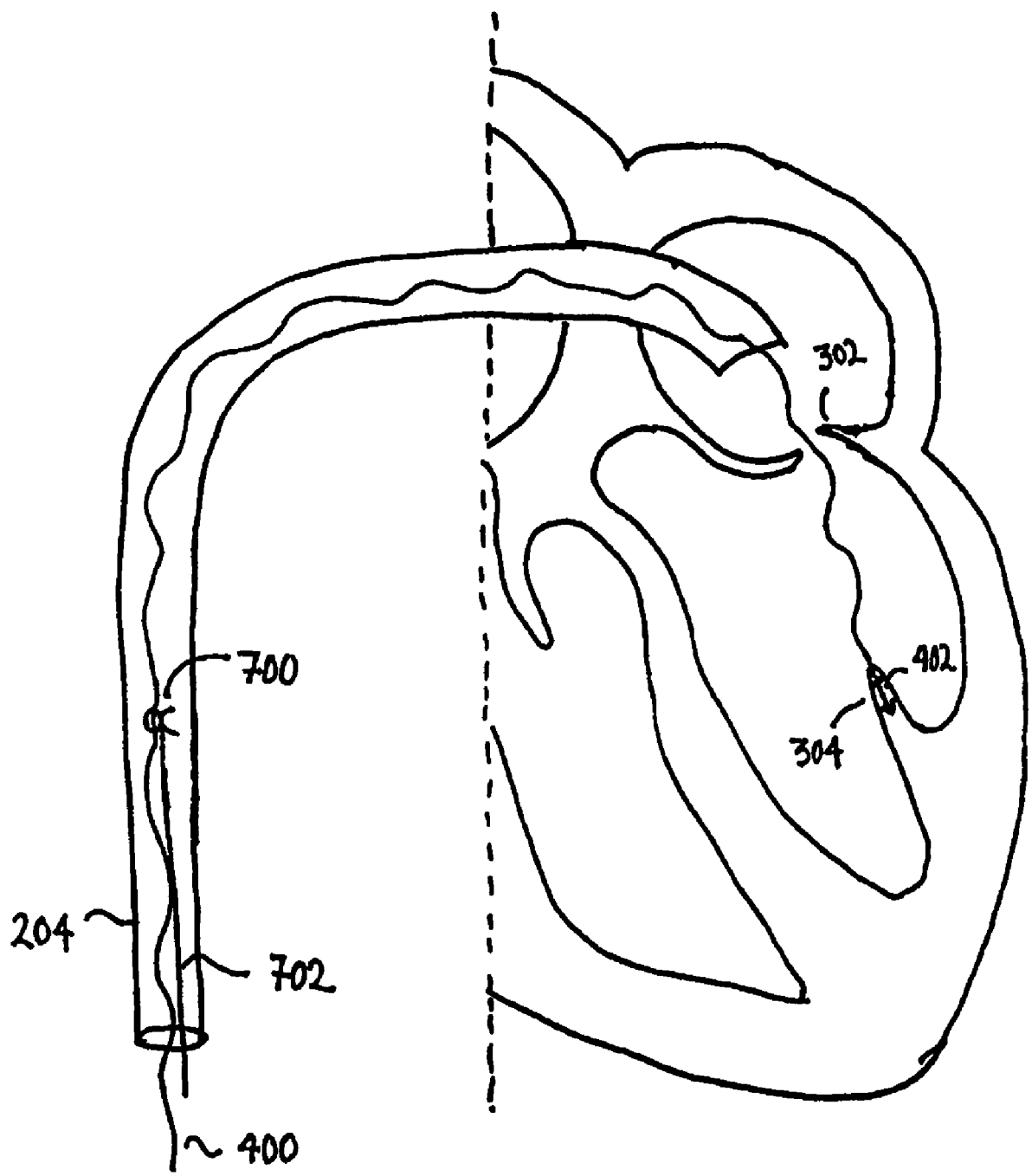
FIG. 7 provides an illustration of the second anchor being advanced to the proximity of the prolapsed mitral valve leaflet.
Figure 9:
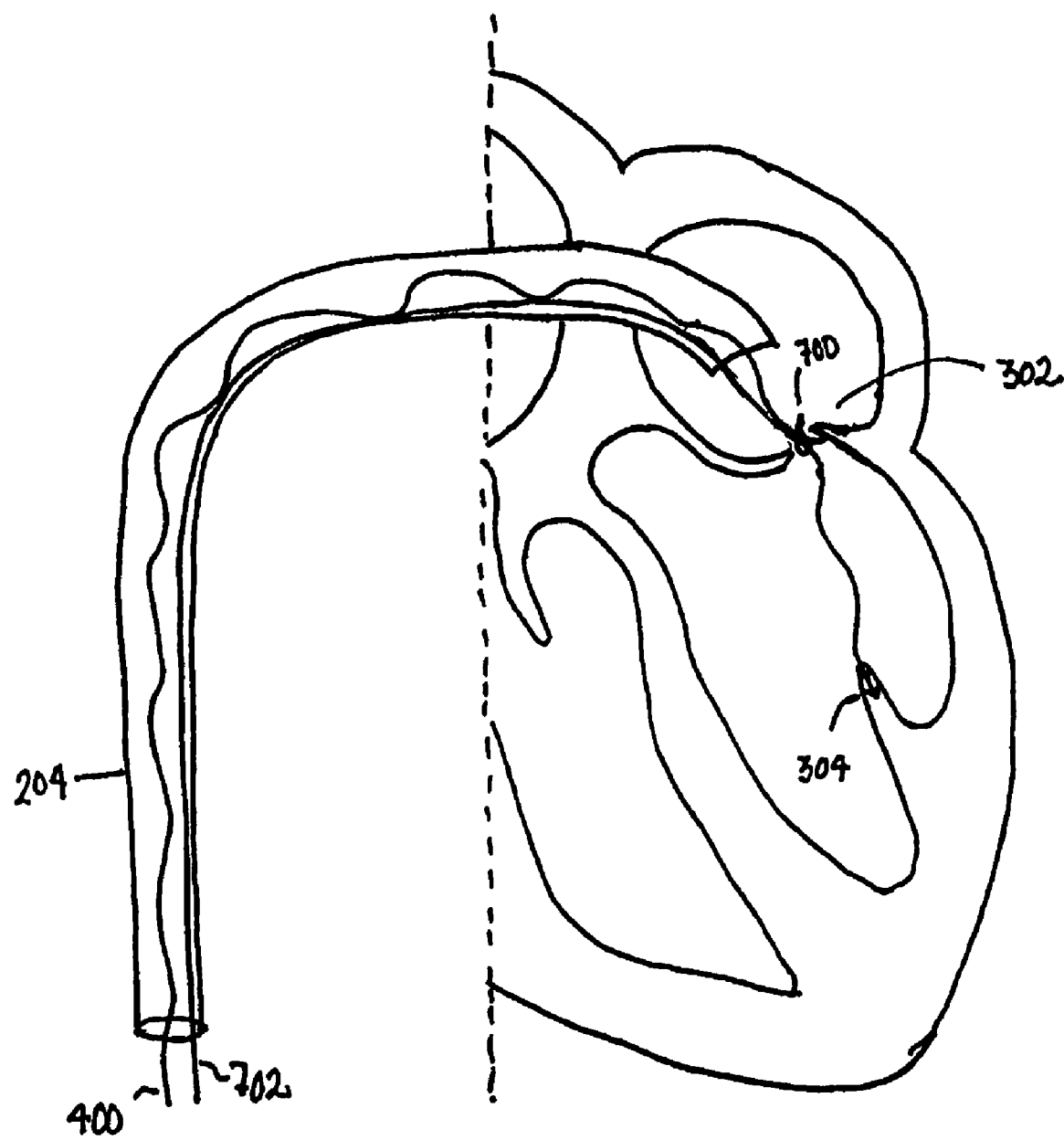
FIG. 9 shows an illustrative method of positioning the second anchor adjacent to the prolapsed mitral valve leaflet.
Figure 10:
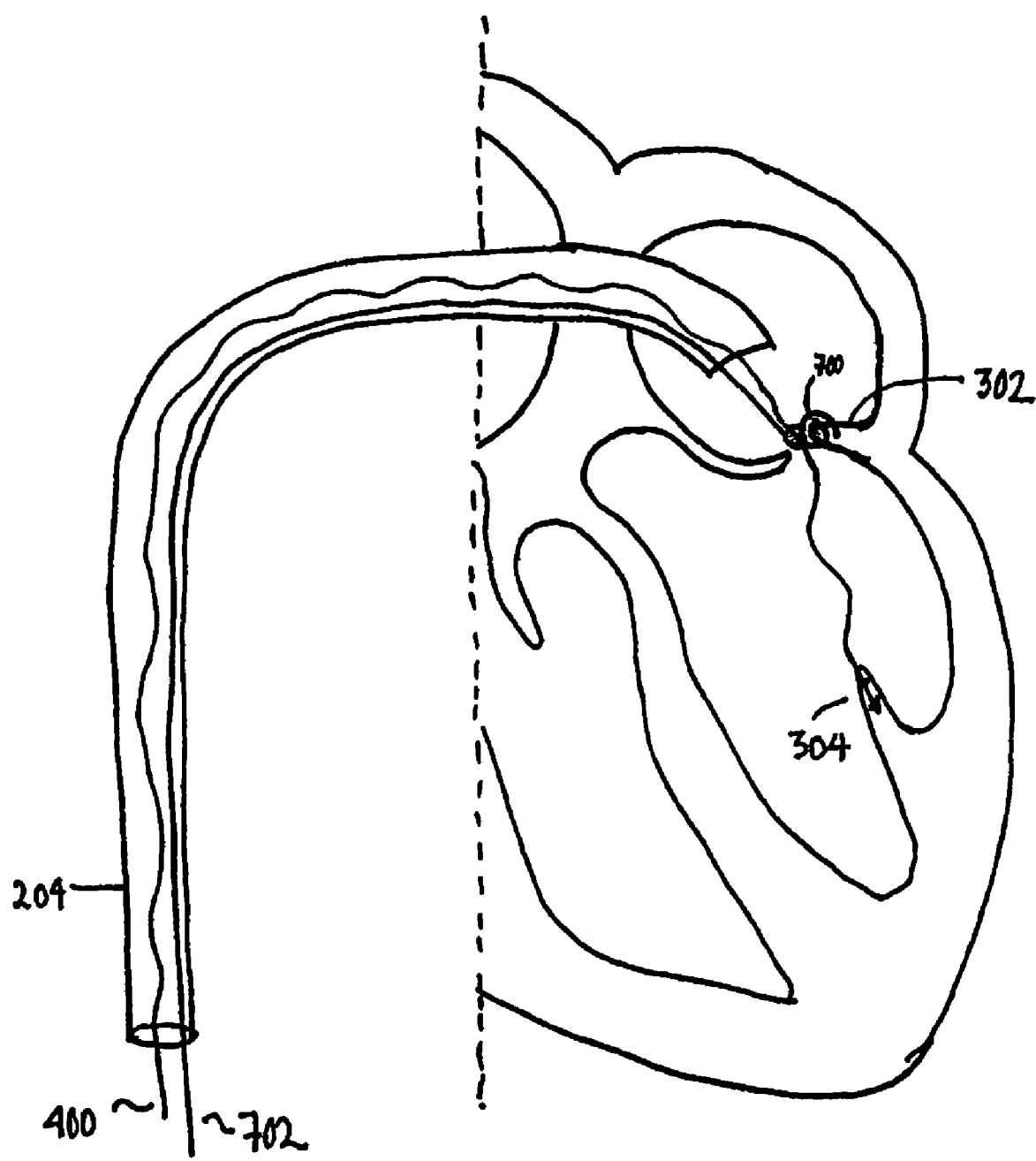
FIG. 10 shows an illustrative method of deploying the second anchor into the prolapsed mitral valve leaflet.

After the first anchor (402) has been firmly secured to cardiac tissue located beneath the prolapsed mitral valve (e.g., into the head of the papillary muscle, 304), the suction to catheter (300) is released, and catheter (300) is withdrawn proximally (shown by arrows), leaving the first anchor (402) attached to cord (400) in place, as shown by FIG. 6. FIG. 7 provides an illustrative depiction of advancement of second anchor (700) along cord (400). Second anchor (700) is slidably attached to the cord (400) and is configured to secure into the prolapsed mitral valve leaflet. The second anchor is typically slid onto the cord (400) proximal of the patient's body, and introduced and advanced to the site of the prolapsed mitral valve with the aid of a catheter (702). In FIGS. 7, 9 and 10, the catheter introducing the anchor is indicated by a line (702). Any appropriate introducer for positioning, releasing and securing the anchor may be used for example, the second anchor may be positioned and released as described above for the first anchor. A practitioner may thread the second anchor onto the cord outside of the body. After the second anchor has been attached to the prolapsed mitral valve leaflet (302), the valve leaflet may be repositioned to correct the prolapse, and tension may be applied to the cord (400) to maintain the proper position of the anchors to correct the prolapse.

Figure 8:
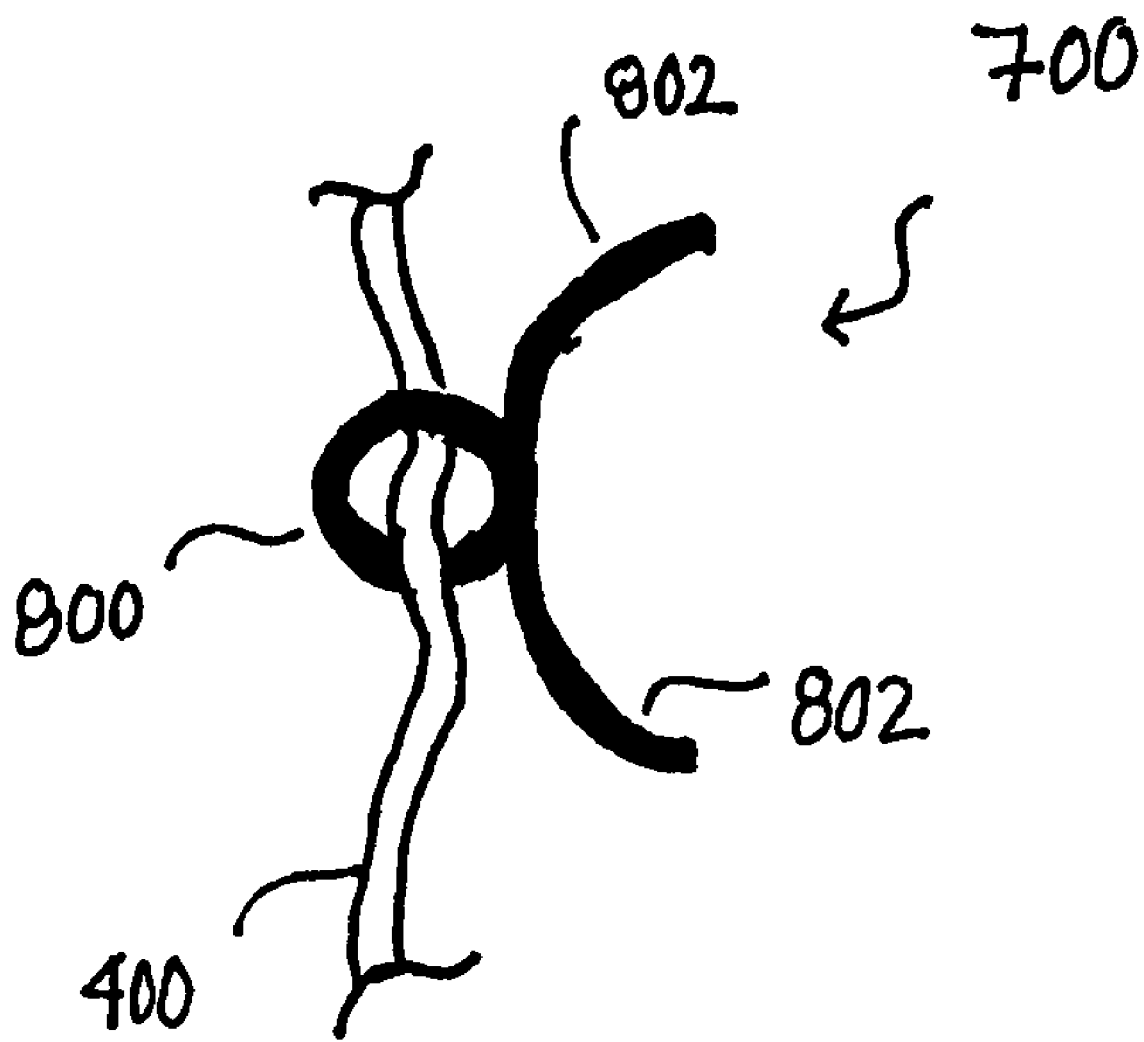
FIG. 8 provides an enlarged view of a suitable second anchor as described herein.

FIG. 8 shows an illustrative depiction of a second anchor (700) in a magnified fashion. Shown there is anchor (700) slidably attached to cord (400). In this variation, second anchor (700) has eyelet (800) allowing for such slidable attachment (i.e., in this variation, the cord is slid through eyelet 800). The second anchor of this variation also has legs (802) that are configured to pierce tissue, and preferably, the tissue of a prolapsed mitral valve leaflet. Again, the legs of the second anchor need not terminate in sharp or otherwise pointed distal tips, so long as the anchor has been suitably designed to pierce tissue. Similarly, as with the first anchor described in detail above, the second anchor may be made of any suitable material, and be of a size suitable to secure into a prolapsed mitral valve leaflet. For example, in some variations the anchor is between about 4 mm and about 8 mm (e.g., the tips of the legs span between about 4 mm and about 8 mm). In some variations, the anchor is about 6 mm.

As noted above, the second anchor (700) may be advanced to prolapsed mitral valve leaflet (302) via catheter (702). Catheter (702) is typically steerable, or otherwise maneuverable so that it can be maneuvered through trans-septal catheter (204) and to the prolapsed mitral valve leaflet (302). Visualization techniques, such as fluoroscopy may be useful in this respect. The second anchor may be attached to the catheter, and released only after it has been attached to the valve leaflet. In some variations, the second anchor may pierce (e.g., pass completely through) the valve leaflet when the second anchor is secured to the valve leaflet. For example, the second anchor may be positioned by abutting the valve leaflet with one or more of the anchor legs, so that the practitioner can cause the anchor legs to penetrate into the valve leaflet. The anchor may be secured to the margin (e.g., within about 5 mm from the edge of the leaflet) or in any other appropriate region of the valve leaflet. In the variation shown in FIG. 9, the legs of anchor (700) are positioned so that they may be inserted into the valve leaflet. For example, the legs may straddle the edge of prolapsed mitral valve leaflet, or one of the legs may hook onto the mitral valve leaflet (302). The second anchor (700) should preferably be positioned at the edge of the mitral valve leaflet, but the legs of the anchor may secure into a deeper margin of the prolapsed mitral valve leaflet if desirable. In some variations, it may be preferable for the practitioner to hook the lower edge of the prolapsed mitral valve leaflet with the lower leg of the second anchor, before the legs are collapsed or expanded (as the case may be) into the leaflet tissue.

FIG. 10 provides an illustrative depiction of the second anchor (700) deployed into the prolapsed mitral valve leaflet (302). The deployment of second anchor (700) may occur in any number of ways. For example, a release mechanism may be activated from outside the patient's body. For example, the release mechanism may comprise a reversibly releasable latch within catheter (702). Having a reversible latch, for example, may be quite beneficial so that the practitioner may have multiple tries at deploying the second anchor, if the first try results in misplacement. The release mechanism, may be made of a cable with a releasable latch at its distal end, for example, or something similar. As described above, the legs of the anchor may be deployed into the tissue by changing the configuration of a shape-memory material or by releasing from a loading configuration (e.g., compressed) into a delivery (e.g., expanded) configuration.

As described above, the legs of the second anchor can be secured into the prolapsed valve leaflet by any suitable mechanism. For example, the second anchor may be made from a self-expanding material, such as a shape memory material (e.g., a nickel titanium alloy), such that, when it is released, its legs expand (or compress or collapse as the case may be) into the tissue of the mitral valve leaflet. Similarly, an expandable balloon may be used to force the legs of the anchor into the prolapsed mitral valve leaflet tissue.

Figure 11:
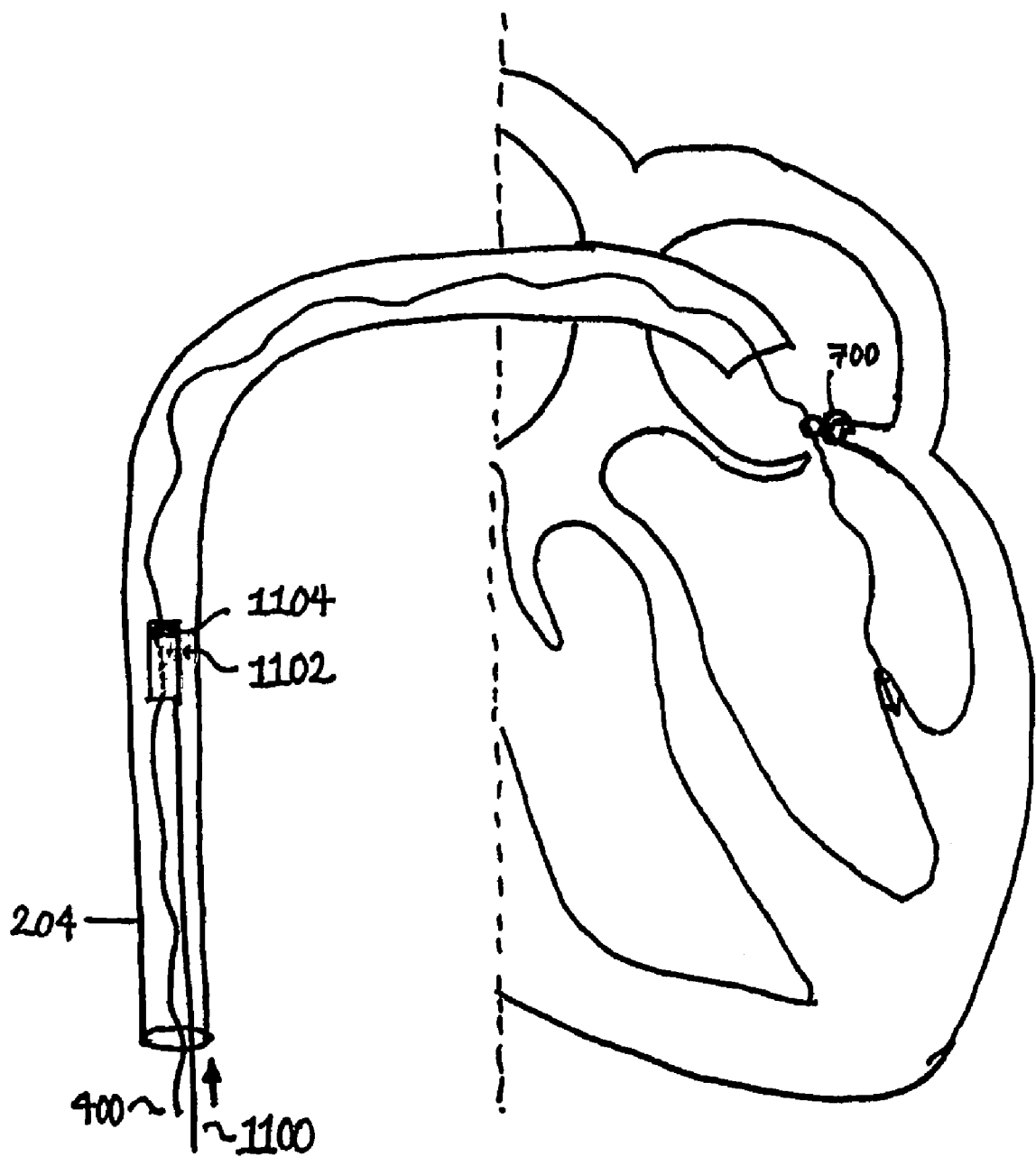
FIG. 11 provides an illustrative depiction of the advancement of a third catheter carrying a fastener.
Figure 12:
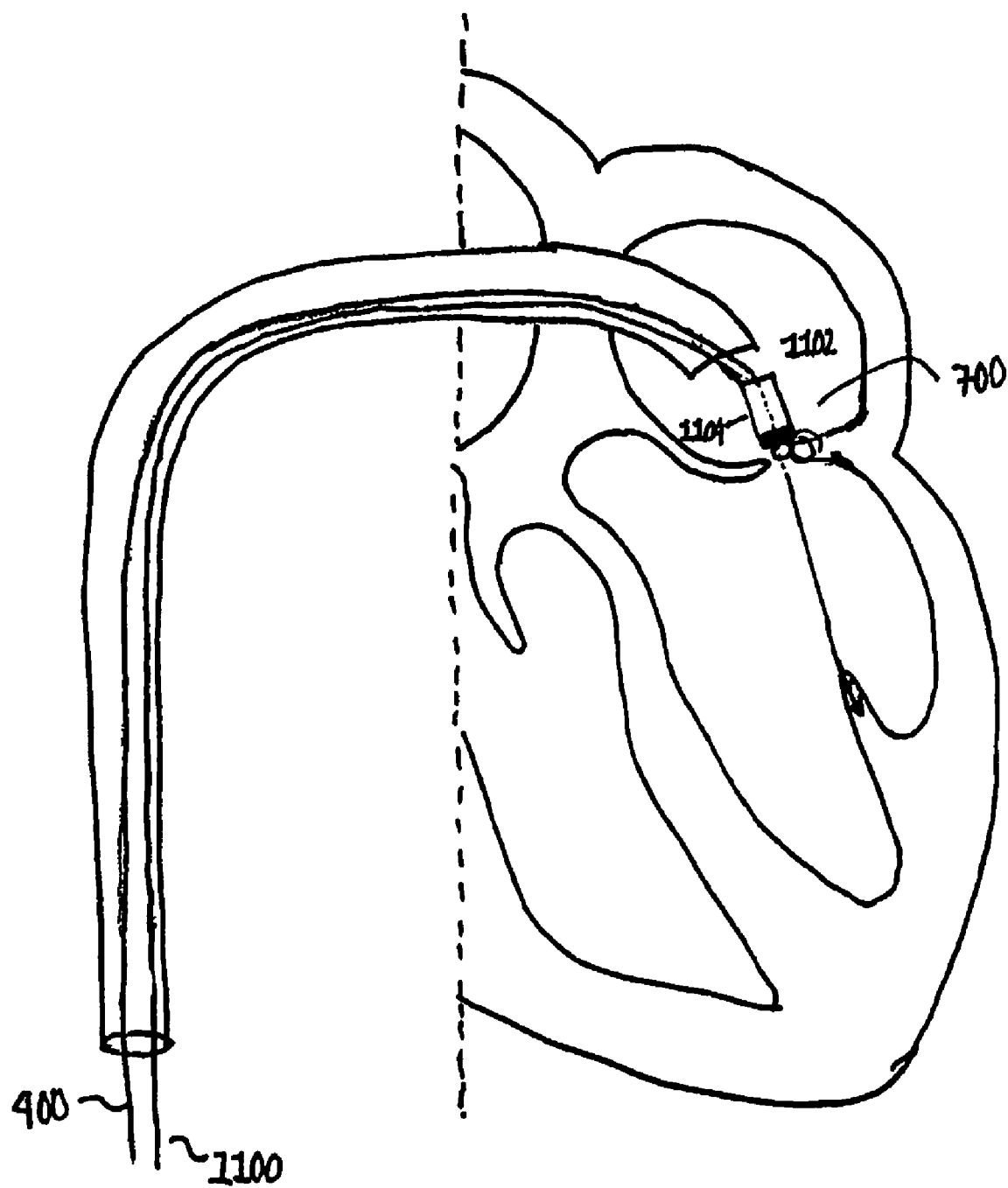
FIG. 12 shows the fastener being positioned and deployed adjacent to the second anchor, after the prolapsed valve has been positioned and the cord has been pulled to tension the cord so that the prolapse has been corrected.

FIG. 11 shows a schematic representation of a catheter (1100) having a releasable fastener (1104) at its distal end (1102) being advanced distally through trans-septal catheter (204). As shown, the distal end (1102) and releasable fastener (1104) have lumens therethrough, which allow them to be thread or slid over cord (400). Catheter (1100) is advanced distally as shown by the arrows, and will be advanced until the releasable fastener (1104) is positioned immediately adjacent to the second anchor (700) as shown by FIG. 12. The position of the valve leaflet is then adjusted (e.g., to correct the prolapse and eliminate mitral regurgitation). Thus, the fastener (1104) may be used to position the valve leaflet. For example, the fastener may be used to push against the second anchor (700) (e.g., by pushing against the eyehole of the fastener). At the same time, the cord (400) can be tensioned to correct the position of the valve leaflet. This position can be maintained by securing the cord (e.g., with the fastener (1104)). A practitioner may adjust the position of the valve leaflet (e.g., by adjusting the position of the fastener and the tension of the cord) while visualizing the heart to correct a prolapse. Correction is obtained when regurgitation into the left atrium disappears or is significantly reduced. The correction can be monitored, for example, by intracardiac echo or transesophageal echo. Thus, the position of the valve leaflet can be adjusted in real time while monitoring any regurgitation. Once the position is optimized, the fastener (1104) may be secured.

As described above, the releasable fastener may be positioned to optimally tension the cord (400) so that the distance between the anchors adequately corrects the position of the prolapsed leaflet. The releasable fastener is then released and fastened or crimped to the cord (400) to secure the cord in this position.

The prolapsed leaflet may be repositioned to correct the prolapse by the practitioner manipulating the valve leaflet, and by applying tension (e.g., pulling) on the cord. In some variations, the practitioner may use a separate manipulator to move the valve leaflet and to secure the cord position. For example, a wire or another catheter (e.g., separate from the catheter used to deliver the fastener) may be used to push against the leaflet or anchor.

Figure 13:
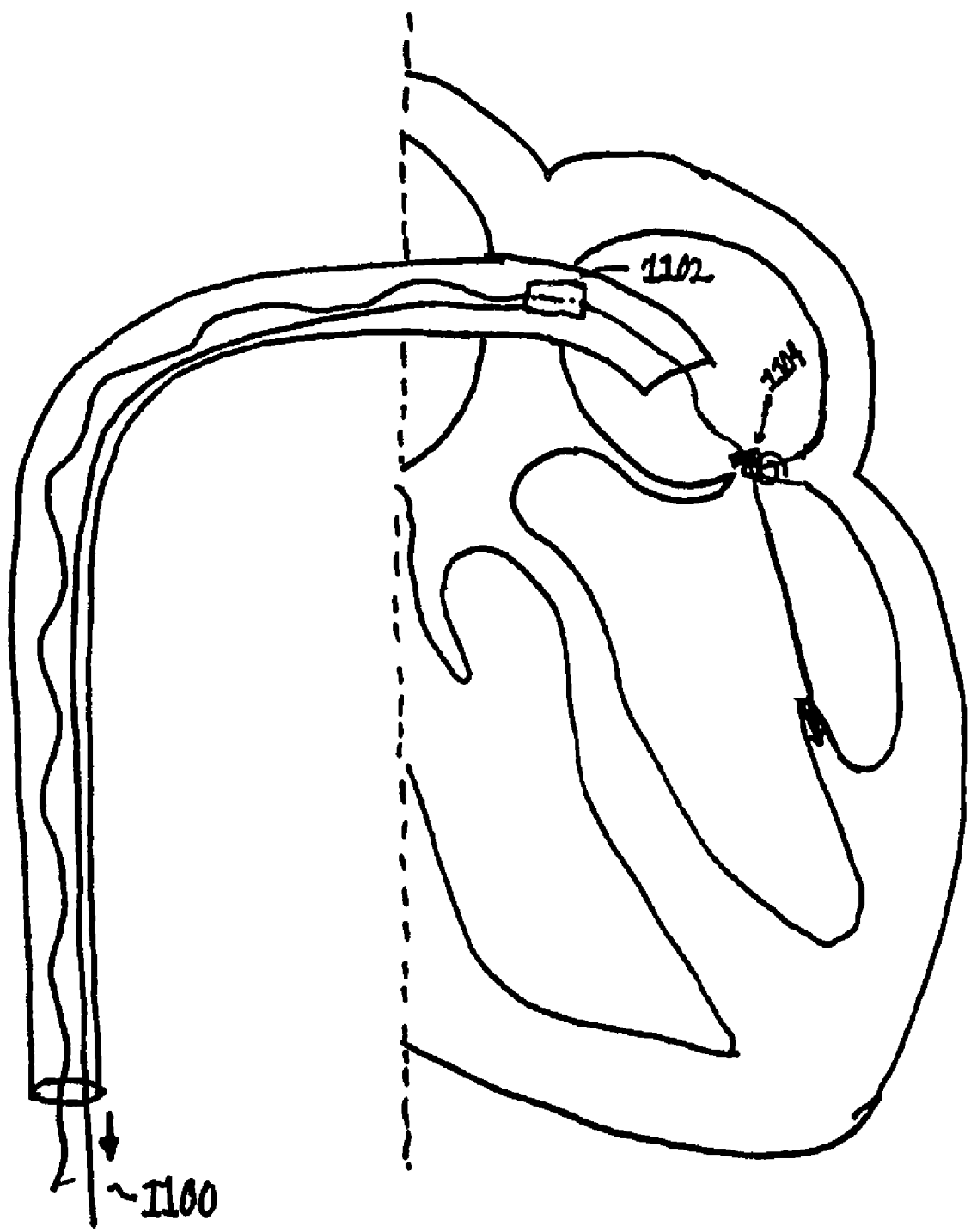
FIG. 13 shows the release of the fastener and removal of the third catheter.

The fastener may be released and secured (e.g., crimped) in any suitable way. For example, the fastener may be held in catheter (1102) by a sheath, and once the sheath is removed, the fastener may be released. Similarly, the fastener may be attached to the catheter by an electrolytic joint, and once it is desired to detach the fastener, electricity may be applied to sever the joint via electrolysis. The fastener may also be released via the use of a push-pull wire. Any number of suitable techniques may also be used with respect to crimping of the fastener. For example, the fastener may be made of a self-collapsing material, such as a shape memory material, that would collapse tightly upon itself after being released. An expandable balloon may also be used to crimp the fastener. That is, as the expandable balloon is inflated, the fastener is crimped tightly upon itself under the pressure. After the fastener is positioned and crimped in place, catheter (1102) is withdrawn proximally as shown by FIG. 13.

Figure 14:
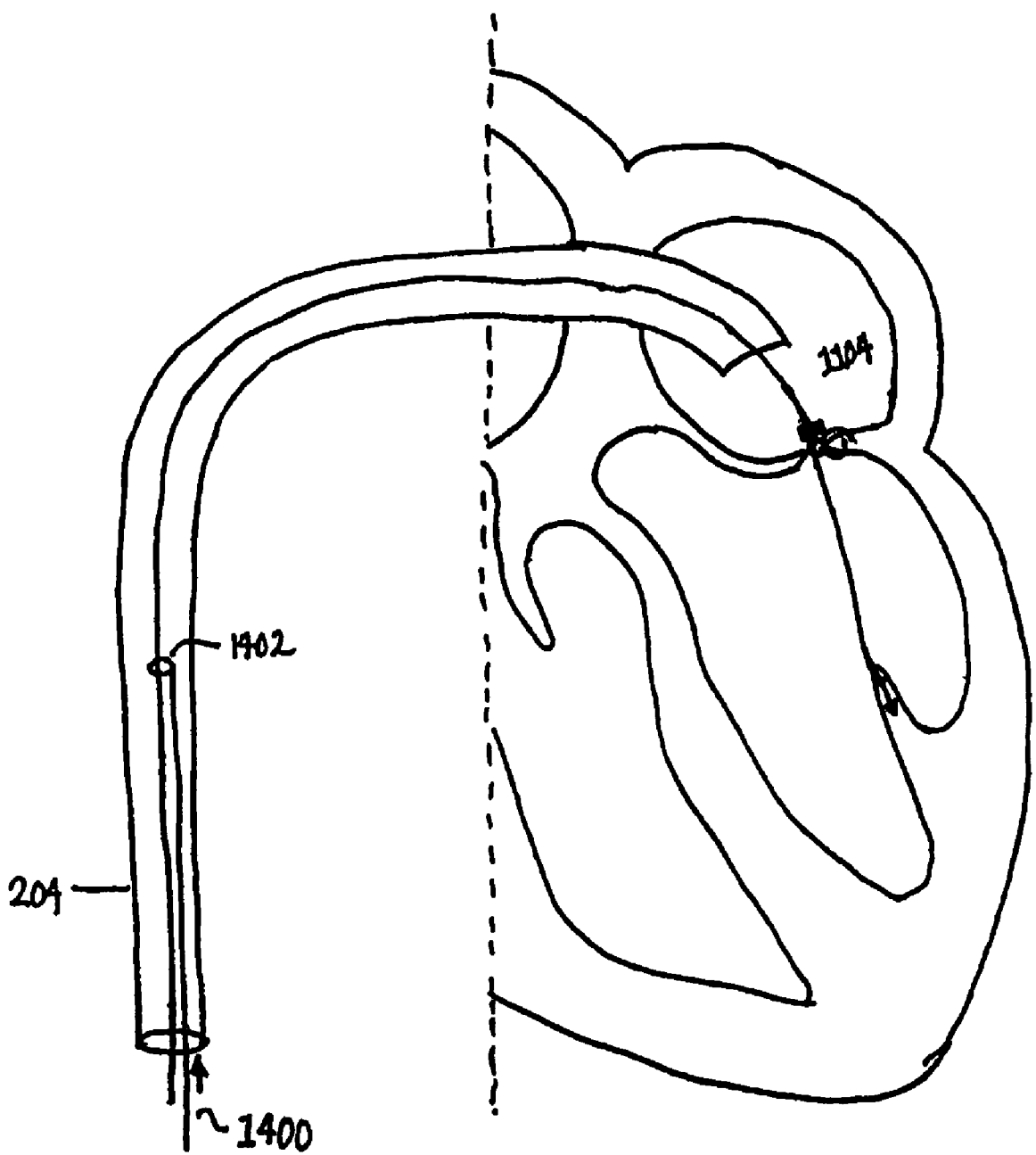
FIG. 14 provides an illustrative depiction of the advancement of a cutting wire.
Figure 15:
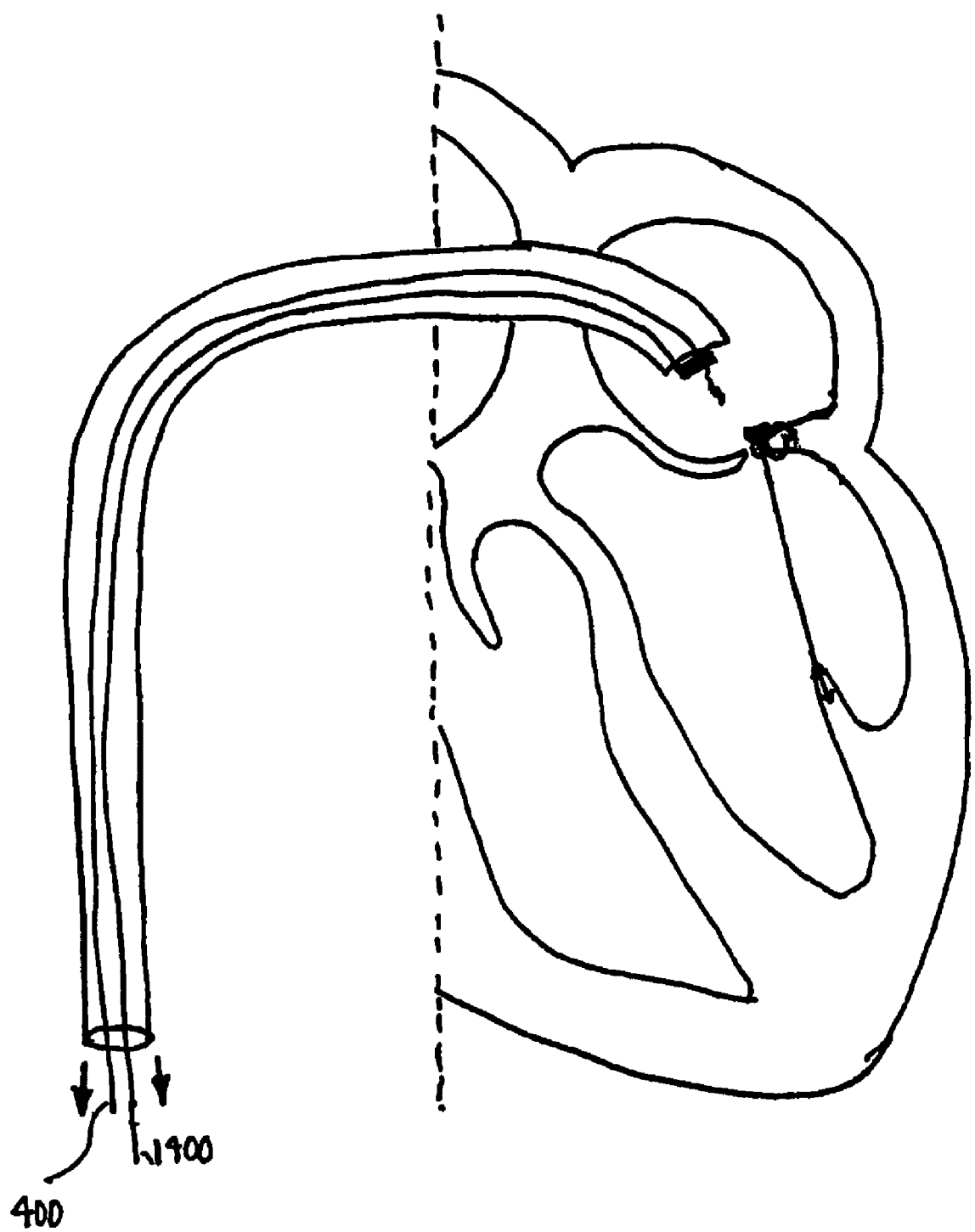
FIG. 15 shows the removal of the cutting wire after excess cord has been cut immediately proximal to the fastener.
Figure 16A:
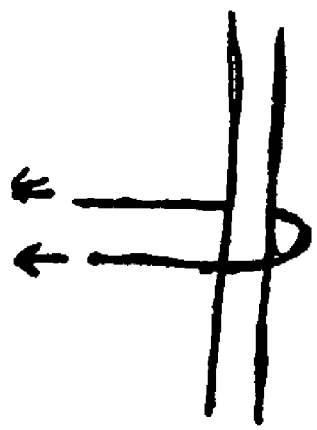
FIGS. 16A-16C illustrate a cutting wire cutting a cord.
Figure 16B:
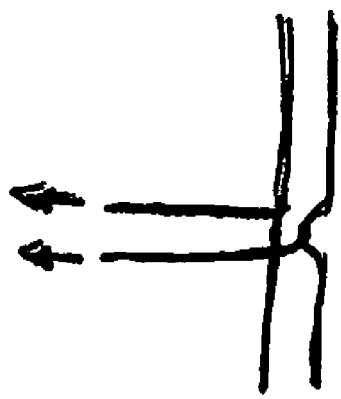
Figure 16C:
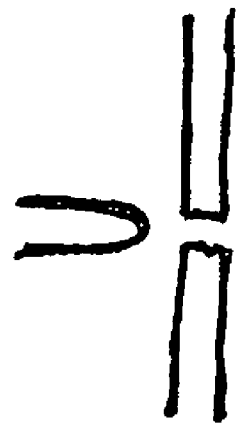

After the prolapse has been corrected via the tightening and securing of the cord, the excess cord remaining in the heart must be cut and removed from the body. This may be accomplished in any number of ways. For example, a cutting catheter (1400) may be advanced distally through trans-septal sheath (204) as shown in. FIG. 14. As shown in that figure, cutting catheter (1400) has a cutting mechanism (1402) at its distal end. The cutting mechanism may be any suitable mechanism, and in the variation shown in FIG. 14, it is a cutting wire having a loop. In this variation, the looped cutting wire is slid over the cord (400) and advanced immediately proximal to the fastener (1104). The looped cutting wire may be made of any suitable biocompatible cutting material, e.g., stainless steel and the like. FIGS. 16A-16C illustrate a cutting wire cutting a cord. The excess cord is cut off, and both the excess cord (400) and the cutting catheter (1400) are removed proximally as shown by FIG. 15. The cord may also be cut at the same time that the fastener is secured and/or released. For example, the same device that deploys the fastener may also cut the cord. In some variations, the cord is cut at the same time that the fastener is secured and/or released.

It should be noted that while the descriptions of the methods herein have focused on repair of mitral valve prolapse, the methods need not be so limited in application. For example, the methods may be used to correct tricuspid valve prolapse, or to provide a tensioned cord between any two areas of tissue requiring such. In addition, while the methods described here focused on a percutaneous trans-septal access, any method of accessing the prolapsed valve is suitable, as noted above.

Kits

Kits for treating a mitral valve prolapse are also provided. In general, the kits comprise a flexible cord, having a proximal end and a distal end, a first anchor attached to the cord at its distal end and configured to secure the cord to cardiac tissue located below the prolapsed mitral valve leaflet, a second anchor for slidabe attachment to the cord, wherein the second anchor is configured to secure into a the prolapsed mitral valve leaflet, and at least one catheter for delivery of the flexible cord to the proximity of the prolapsed mitral valve leaflet. Additional catheters may be included in the kits as well.

Any number of appropriate catheters may be used with devices and methods described herein, and may be included as part of a kit. For example, individual catheters may be used to deliver and/or implant the first anchor and cord, to delivery and/or implant the second anchor, to reposition the valve leaflet, or to deliver and/or secure a fastener for the cord.

Additional catheters may also be included. In some variations, catheters may be combined. For example, a single catheter may be used to deliver and/or implant the second anchor and to reposition the leaflet. Thus, any of the catheters may be combined.

In addition, as evidenced by the description of the methods above, it may be advantageous to provide a kit with additional tools useful in carrying out the described methods. For example, the kits may further comprise a cutting wire for cutting the cord, and/or a fastener. The kit may also include instructions on how to use the contents of the kit. Instructions may include reference materials (including indications for use, etc.) and be in any appropriate format, including written, pictographic, visual, electronic, etc., and be in any language, or multiple languages.

As with the devices described above, at least one of the first or second anchors may be made from a shape memory material, such as a nickel titanium alloy. The first anchor may have a tissue piercing tip, which may further comprise two legs that may or may not be configured to expand into cardiac tissue. Similarly, the cord may be made from a material selected from the group consisting of non-polymeric fabrics, polymers, and mixtures thereof. In some variations, the cord is made from a non-polymeric fabric and polymer mixture, such as a PTFE fabric.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention.

What is claimed is:

1. A method for treating a prolapsed mitral valve leaflet comprising:
    advancing a flexible cord, having a first anchor attached at its distal end to the proximity of the prolapsed mitral valve leaflet;
    securing the first anchor to cardiac tissue located below the prolapsed mitral valve leaflet;
    securing a second anchor slidably attached to the cord into the prolapsed mitral valve leaflet;
    tensioning the cord after the second anchor has been secured into the prolapsed mitral valve leaflet; and
    cutting the cord comprising advancing a looped cutting wire over the cord; positioning the looped cutting wire proximal of the second anchor; and pulling on the cutting wire to cut the cord.

2. The method of claim 1 further comprising fixing the cord in its tensioned position.

3. The method of claim 2 wherein fixing the cord further comprises applying a fastener to the cord.

4. The method of claim 1 wherein the cardiac tissue is selected from the group consisting of a papillary muscle and a ventricular wall.

* * * * *